United States Patent
Zhang

(10) Patent No.: US 11,535,656 B2
(45) Date of Patent: Dec. 27, 2022

(54) CYTOKINE COMBINATION

(71) Applicant: Jinyu Zhang, Chongqing (CN)

(72) Inventor: Jinyu Zhang, Chongqing (CN)

( * ) Notice: Subject to any disclaimer, the term of this patent is extended or adjusted under 35 U.S.C. 154(b) by 0 days.

(21) Appl. No.: 16/500,429

(22) PCT Filed: Mar. 26, 2018

(86) PCT No.: PCT/CN2018/080479
§ 371 (c)(1),
(2) Date: Oct. 3, 2019

(87) PCT Pub. No.: WO2018/184484
PCT Pub. Date: Oct. 11, 2018

(65) Prior Publication Data
US 2020/0199189 A1    Jun. 25, 2020

(30) Foreign Application Priority Data

Apr. 6, 2017    (CN) .......................... 201710221755.8

(51) Int. Cl.
| | |
|---|---|
| C07K 14/54 | (2006.01) |
| A61P 35/00 | (2006.01) |
| C07K 14/52 | (2006.01) |
| C07K 14/535 | (2006.01) |
| C07K 14/55 | (2006.01) |
| A61K 38/20 | (2006.01) |
| A61K 38/19 | (2006.01) |
| A61P 35/04 | (2006.01) |
| A61K 9/00 | (2006.01) |
| A61K 38/00 | (2006.01) |

(52) U.S. Cl.
CPC ........ *C07K 14/5434* (2013.01); *A61K 38/193* (2013.01); *A61K 38/208* (2013.01); *A61P 35/00* (2018.01); *A61P 35/04* (2018.01); *C07K 14/52* (2013.01); *C07K 14/535* (2013.01); *C07K 14/54* (2013.01); *C07K 14/55* (2013.01); *A61K 9/0014* (2013.01); *A61K 38/00* (2013.01); *C07K 14/5418* (2013.01); *C07K 14/5443* (2013.01)

(58) Field of Classification Search
None
See application file for complete search history.

(56) References Cited

U.S. PATENT DOCUMENTS

| | | |
|---|---|---|
| 2012/0164101 A1 | 6/2012 | Galipeau et al. |
| 2016/0022812 A1 | 1/2016 | Mitsunaga et al. |

FOREIGN PATENT DOCUMENTS

| | | |
|---|---|---|
| CN | 104630145 A | 5/2015 |
| CN | 106520778 A | 3/2017 |
| EP | 0815245 | 8/1996 |
| EP | 1731531 | 12/2006 |
| WO | 0110912 | 2/2001 |
| WO | 2015124297 | 8/2015 |

OTHER PUBLICATIONS

Spangler et al (Annu Rev Immunol. Mar. 21, 2015; 33: 139-167) (Year: 2015).*
Miosge et al (Proc Natl Acad Sci U S A. Sep. 15, 2015;112(37):E5189-98) (Year: 2015).*
Lee et al (Nat Rev Mol Cell Biol. Dec. 2007;8(12):995-1005) (Year: 2007).*
Bowie et al. (Science, 1990, 247:1306-1310) (Year: 1990).*
Lazar et al. (Mol. Cell. Biol., 8:1247-1252, 1988) (Year: 1988).*
Bork (Genome Research, 2000,10:398-400) (Year: 2000).*
Burgess et al. (J. Cell Biol. 111:2129-2138, 1990) (Year: 1990).*
Orsi et al (Animal Reproduction Science 100 (2007) 301-310) (Year: 2007).*
Kilinc et al (J Immunol 2006; 177:6962-6973) (Year: 2006).*
Hill et al (Cancer research (2002) 62, 7254-7263) (Year: 2002).*
Wen et al (J Transl Med (2016) 14:41) (Year: 2016).*
Li, Lan, Effects of IL-21 Alone or in Combination with IL-15/IL-2 on Proliferation and Anti-tumor Activity of G-CSF-Mobilized Peripheral Blood Mononuclear Cells in Vitro, Journal of Experimental Hematology, Dec. 31, 2008, 16 (2), pp. 350-354.
International Search Report for PCT/CN2018/080479 dated Jun. 8, 2018.
Chang, Chun-Jung, et al., Combined GM-CSF and IL-12 Gene Therapy Synergistically Suppresses the Growth of Orthotopic Liver Tumors, Hepatology, vol. 45, No. 3., 2007, pp. 746-754.
Indrova, Marie, et al., Chemoimmunotherapy in mice carrying HPV16-associated, MHC class I+ and class I-tumours: effects of CBM-4A potentiated with IL-2, IL-12, GM-CSF and genetically modified tumour vaccines, Intl J of Oncology, 22:691-695, 2003.

(Continued)

*Primary Examiner* — Brian Gangle
*Assistant Examiner* — Andrea K McCollum
(74) *Attorney, Agent, or Firm* — Honigman LLP; Thomas A. Wootton, Esq.; Jonathan P. O'Brien

(57) ABSTRACT

Provided is a cytokine combination for treating a tumor and/or preventing recurrence or metastasis of the tumor. The cytokine combination comprising at least three cytokines selected from the following groups: IL(interleukin)12 or a functional variant thereof, GMCSF (granulocyte-macrophage colony-stimulating factor) or a functional variant thereof, FLT3L (FMS-like tyrosine kinase 3 ligand) or a functional variant thereof, IL2 or a functional variant thereof, IL15 or a functional variant thereof, IL21 or a functional variant thereof, and IL7 or a functional variant thereof. Also provided is a nucleic acid molecule encoding the cytokine combination and a vector thereof, a cell, a pharmaceutical composition, and a application thereof for the manufacture of a drug for treating the tumor and/or preventing recurrence or metastasis of the tumor.

14 Claims, 16 Drawing Sheets

Specification includes a Sequence Listing.

(56) References Cited

OTHER PUBLICATIONS

Jean, Walter C., et al., Effects of combined granulocyte-macrophage colony-stimulating factor (GM-CSF), interleukin-2, and interleukin-12 based immunotherapy against intracranial flioma in the rat, J of Neuro-Oncology, 66: 39-49, 2004, Kluwer Academic Publishers.
Kaufmann, Howard L., et al., Insertion of interleukin-2 (IL-2) and interleukin-12 (IL-12) genes into vaccinia virus results in effective anti-tumor responses without toxicity, Vaccine 20, 2002, 1862-1869, Elsevier.
Zhang, Jinyu, et al., Administration of fusion cytokines induces tumor regression and systemic antitumor immunity, MedComm, Wiley, 2021; 2: 256-268.

* cited by examiner

| 4T1 | | CT26 | |
|---|---|---|---|
| Wild mice | Cured mice | Wild mice | Cured mice |
| 2/2 | 0/5 | 2/2 | 0/5 |

CYTOKINE COMBINATION

CROSS-REFERENCE TO RELATED APPLICATIONS

This application is a National Stage Application and claims priority under 35 U.S.C. § 371 to Patent Cooperation Treaty application PCT/CN2018/080479, filed Mar. 26, 2018, which claims the benefit of Chinese Patent Application No. 201710221755.8, filed Apr. 6, 2017, priority is claimed to both of these applications and the disclosures of these prior applications are considered part of the disclosure of this application and to the extent allowed the entire contents of the aforementioned applications are incorporated herein.

SEQUENCE LISTING

This application incorporates by reference in its entirety the Sequence Listing entitled "2019-10-01_262790-454671_Sequence_Listing_ST25.txt," is 24,609 bytes in size and was created on Oct. 1, 2019, and filed electronically herewith.

TECHNICAL FIELD

The present application relates to the field of oncotherapy. Specifically, the present application relates to a cytokine combination containing at least three cytokines and an application thereof in treating tumors and/or preventing the recurrence or metastasis of tumors.

BACKGROUND

In recent years, immunotherapy, a new therapy for treating tumors that pose a huge threat to the health of human beings, demonstrated a tremendous potential in oncotherapy. At the present stage, the leading immunotherapies for tumors include the chimeric antigen receptor T-cell (CAR-T) immunotherapy and the immune checkpoint therapy. The former can more accurately and effectively identify and kill tumor cells in the body by modifying T cells. The immune checkpoint therapy can block signal pathways capable of suppressing T cell functions in the tumor microenvironment through antibody binding, so that T cells can be reactivated to kill tumor cells. However, these two types of therapies are still far from achieving an ideal effect. CAR-T has a poor effect in treating solid tumors, because CAR-T cells can hardly get into the tumor in a large amount due to the dense and strongly-immunosuppressive microenvironment created in a solid tumor. And even if they are inside the tumor, the functions of the CAR-T cells may be suppressed in the tumor microenvironment. The low response rate of the immune checkpoint therapy, generally only about 20-30%, indicates that it may not be sufficient to eliminate a solid tumor in most cases by merely releasing and reactivating T cells. Tumor cells build an immunosuppressive microenvironment inside a tumor by secreting various proteins or by directly contacting and interacting. A variety of immunocytes, including macrophage, regulatory cell (Treg), marrow-derived suppressor cell (MDSC), etc., participate in this process. Cracking the immunosuppressive microenvironment of a tumor is a key for the success of an immunotherapy for a tumor, where the CAR-T therapy and the immune checkpoint therapy both have a limited effect.

Cytokine is very important immune signal in the body. Various cells secrete different cytokines which can act on different cells, forming a complex cross-network, and moreover, the same cytokine can act on different cells in different environments, thereby exerting completely opposite function. All existing cytokines or combinations thereof, which have been used, haven't shown fully satisfactory results in treating tumors.

SUMMARY

The present application provides a cytokine combination containing specific cytokines and a pharmaceutical composition thereof.

In one aspect, the present application provides a cytokine combination containing at least three cytokine selected from the following groups: IL12 or a functional variant thereof, GMCSF or a functional variant thereof, FLT3L or a functional variant thereof, IL2 or a functional variant thereof, IL15 or a functional variant thereof, IL21 or a functional variant thereof, and IL7 or a functional variant thereof.

In some embodiments, the cytokine combination contains at least one of the following groups: (1) IL12 or a functional variant thereof, GMCSF or a functional variant thereof, and IL2 or a functional variant thereof; (2) IL12 or a functional variant thereof, GMCSF or a functional variant thereof, and IL15 or a functional variant thereof; (3) IL12 or a functional variant thereof, GMCSF or a functional variant thereof, and IL21 or a functional variant thereof; (4) IL12 or a functional variant thereof, FLT3L or a functional variant thereof, and IL2 or a functional variant thereof; (5) IL12 or a functional variant thereof, FLT3L or a functional variant thereof, and IL15 or a functional variant thereof; (6) IL12 or a functional variant thereof, FLT3L or a functional variant thereof, and IL21 or a functional variant thereof; (7) IL12 or a functional variant thereof, GMCSF or a functional variant thereof, and IL7 or a functional variant thereof; (8) IL12 or a functional variant thereof, FLT3L or a functional variant thereof, and IL7 or a functional variant thereof.

In some embodiments, the cytokine are selected from mouse cytokine and human cytokine.

In some embodiments, the concentration of each cytokine in the cytokine combination is 1-10000 ng/µL.

In another aspect, the present application provides one or more nucleic acid molecules encoding the cytokine combination.

In some embodiments, the nucleic acid molecule include more than two nucleic acid molecules, wherein, each of the nucleic acid molecule encodes one or more cytokines, and each of the nucleic acid molecule encodes said cytokine which is different from the cytokine coded by at least one of the other nucleic acid molecule.

In another aspect, the present application provides a vector containing the nucleic acid molecule.

In some embodiments, the vector includes more than two vectors, wherein, each of the vector contains one or more nucleic acid molecule, and the cytokine encoded by the nucleic acid molecule contained in each of the vector is different from the cytokine encoded by the nucleic acid molecule contained in at least one of the other vector.

In another aspect, the present application provides a cell containing the nucleic acid molecule or the vector.

In some embodiments, the cell includes more than two cells, wherein, each of the cell expresses one or more cytokines, and the cytokine expressed by each of the cell is different from the cytokine expressed by at least one of the other cell.

In another aspect, the present application provides a pharmaceutical composition, containing the cytokine combination, the nucleic acid molecule, the vector or the cell, and optionally a pharmaceutically acceptable carrier.

In some embodiments, the pharmaceutical composition is prepared to be suitable for topical administration. In some embodiments, the pharmaceutical composition is prepared to be suitable for slow-release administration. For example, the pharmaceutical composition is prepared in a calcium alginate gel, a polylactic acid microsphere or a chitosan quaternary ammonium salt solution.

In another aspect, the present application provides an application of the cytokine combination, the nucleic acid molecule, the vector, the cell or the pharmaceutical composition in the preparation of drugs for treating a tumor and/or preventing the recurrence or metastasis of a tumor.

In some embodiments, the tumor is solid tumor. In some embodiments, the tumor is selected from the group consisting of lung cancer, esophageal carcinoma, gastric carcinoma, colorectal cancer, liver cancer, breast cancer, cervical cancer, thyroid carcinoma, brain and central nervous system cancer, pancreatic cancer, oral cancer, nasopharyngeal carcinoma, head and neck cancer, laryngeal cancer, bone cancer, skin cancer, ovarian cancer, prostate cancer, testicular cancer, renal carcinoma, bladder cancer, eyelid neoplasm, leukemia and lymphoma.

In some embodiments, the concentration of each cytokine in the cytokine combination is 1-10000 ng/μL.

In some embodiments, the subject is mammal. For example, the mammal is selected from the group consisting of human being, mouse, rat, monkey, dog, pig, sheep, cow and cat.

Those skilled in the art can easily have an insight into other aspects and advantages of the present disclosure from the following detailed description. Only the exemplary embodiments of the present disclosure are showed and described in the following detailed description. The content of the present disclosure enables those skilled in the art to modify the disclosed specific embodiments without departing from the spirit and scope of the invention involved in the present application, as will be appreciated by those skilled in the art. Accordingly, the drawings of the present application and description in the specification are merely intended to be illustrative, rather than for limitation.

BRIEF DESCRIPTION OF THE DRAWINGS

The specific features of the invention involved in the present application are as set forth in the appended claims. The characteristics and advantages of the invention involved in the present application can be better understood by referring to the exemplary embodiments and drawings described in detail below. The brief description of the drawings is as follows:

DETAILED DESCRIPTION

Figure 1:
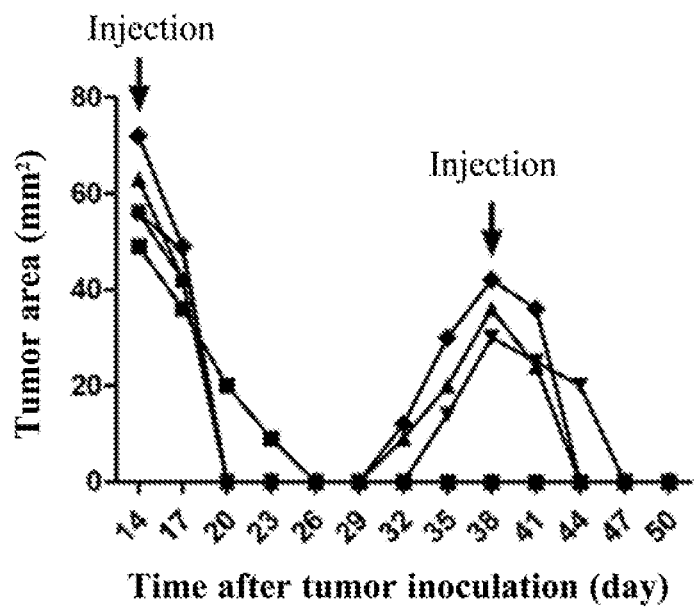
FIG. 1 shows the therapeutic effect of the mIL12+mGMCSF+mIL2 chitosan quaternary ammonium salt solution on the mouse melanoma (B16F10).

The embodiments of the invention of the present application will be described below by way of specific examples. Those skilled in the art can easily appreciate other advantages and effects of the invention of the present application from the disclosure of the specification.

In the present application, the term "functional variant" generally refers to a fragment or variant with the function of a cytokine. For example, the functional fragment or variant can have an amino acid sequence that is obtained by substituting, deleting or adding one or more (such as 1 to 2, 1 to 3, 1 to 4, 1 to 5, 1 to 6, 1 to 7, 1 to 8, 1 to 9, 1 to 10, or more) amino acids on the basis of the amino acid sequence of the cytokine, and still has the function of the cytokine. For another example, the functional fragment or variant can have an amino acid sequence that has at least about more than 80% (such as at least about more than 80%, about more than 85%, about more than 90%, about more than 91%, about more than 92%, about more than 93%, about more than 94%, about more than 95%, about more than 96%, about more than 97%, about more than 98%, about more than 99% or more) of homology with the amino acid sequence of the cytokine, and still has the function of the cytokine. The functional variant may be a natural variant (such as an allelic variant) or an artificially-modified variant. In the present application, the homology has the meaning commonly known in the art, and moreover, a technique disclosed can be utilized to calculate the percentage of sequence homology between two nucleic acids or polypeptide molecules or domains, for example, a sequence homology can be determined along the full lengths of polynucleotides or polypeptides or alone the domains of the molecules (for example, see Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). The method for determining the level of homology between two polynucleotides or polypeptides is well-known by those skilled in the art (for example, see Carrillo, H. & Lipman, D., SIAM J Applied Math 48:1073 (1988)). In the present application, the bioactivity of an obtained polypeptide substantially remains unchanged when a single amino acid (such as, appropriate conservative amino acid) in the non-essential domain of the polypeptide is substituted (for example, see Watson et al., Molecular Biology of the Gene, 4th Edition, 1987, The Benjamin/Cummings Pub. co., p. 224). In the present application, the functional variant can be obtained through separation from a natural source thereof, recombinant expression or chemical synthesis. For example, a functional variant of a cytokine can be prepared to prolong the half-life of the cytokine or a cytokine combination in the body. For example, a polyethylene glycol (PEG) group is added onto the cytokine.

In the present application, the term "cytokine" generally refers to a small-molecule polypeptide which is mainly secreted by immunocytes and can regulate cell functions. Cytokines play an important role in regulating the interaction between cells, as well as the growth and differentiation of cells. For example, the cytokine can be selected from one or more of the group consisting of interleukin and colony-stimulating factor. In the present application, the interleukin is a kind of cytokine that is produced by a variety of cells and acts on a variety of cells, and initially, merely refers to a cytokine that is produced by leukocytes and plays a role among leukocytes. The interleukin plays an important role in the transmission of information, the activation and regulation of immunocytes, the mediation of activation, proliferation and differentiation of T and B cells, and inflammatory response, and the interleukin known at present includes IL1-IL38. For example, the interleukin can be selected from one or more of the group consisting of IL12, IL2, IL15, IL21 and IL7. In the present application, the colony-stimulating factor refers to a cytokine that can stimulate different hematopoietic stem cells to form cell colonies in semisolid media. The colony-stimulating factor promotes the proliferation and differentiation of hematopoietic stem cells at different stages of development. For example, according to the coverages of colony-stimulating factors, the colony-stimulating factors can be named as granulocyte colony-stimulating factor (G-CSF), macrophage colony-stimulating factor (M-CSF), granulocyte-macrophage colony-stimulating factor (GM-CSF), and multi-colony stimulating factor (multi-CSF, IL3). For example, the colony-stimulating factor can be selected from one or more of the group consisting of FMS-related tyrosine kinase 3 ligand (FTL3L) and granulocyte-macrophage colony stimulating factor (GMCSF).

In the present application, the term "IL2" generally refers to interleukin-2 which plays an important role in the immune response and antiviral infection mechanism of the body. IL2 can stimulate the proliferation of T cells that have been activated by a specific antigen, activate T cells and promote the secretion of cytokines; IL2 can also stimulate the proliferation of NK cells, enhance the killing activity of NK, promote the production of cytokines and induce the production of LAK cells; IL2 can also facilitate B cells to proliferate and secrete an antibody; and, activate macrophages. For example, mouse IL2 (mIL2) can contain an amino acid sequence shown as SEQ ID NO: 5. For another example, human cytokine IL2 (hIL2) can contain an amino acid sequence shown as SEQ ID NO: 12.

In the present application, the term "IL12" generally refers to interleukin-12. IL-12 can stimulate the proliferation of activated T cells and promote the differentiation of Th0 cells into Th1 cells; IL-12 can also induce the cytotoxic activity of CTL and NK cells, and promote them to secrete IFN-γ, TNF-α, GM-CSF and other cytokines; or IL-12 can promote the expression of NK cells and IL-2Rα receptors and CD56 molecules, and enhance the ADCC effect on tumor cells. The molecule of IL12 is a heterodimer, and the p40 subunit (40kd) and the p35 subunit (35kd) are linked to each other through a disulfide bond. For example, the p35 subunit in mouse IL12 (mIL12) can contain an amino acid sequence shown as SEQ ID NO: 1, and the p40 subunit can contain an amino acid sequence shown as SEQ ID NO: 2. For another example, the p35 subunit in human IL12

(hIL12) can contain an amino acid sequence shown as SEQ ID NO: 8, and the p40 subunit can contain an amino acid sequence shown as SEQ ID NO: 9.

In the present application, the term "IL15" generally refers to interleukin-15, which is generated by a variety of cells, such as activated mononuclear macrophages, epidermal cells, fibroblasts, etc. IL15 can induce the proliferation and differentiation of B cells, and exert a biological activity similar to that of IL2. For example, mouse IL15 (mIL15) can contain an amino acid sequence shown as SEQ ID NO: 6. For another example, human IL15 (hIL15) can contain an amino acid sequence shown as SEQ ID NO: 13.

In the present application, the term "IL7" generally refers to interleukin-7, which is mainly secreted by stromal cells in the thymus and bone marrow. IL7 belongs to the glycoproteins with a relative molecular weight of 25000-28000. Signal transduction pathways mediated by IL7 and receptors thereof are mainly achieved by three pathways, i.e. Janus kinase, signal transducers and activators of transcription, and phosphoinositide 3-kinase. For example, mouse IL7 (mIL7) can contain an amino acid sequence shown as SEQ ID NO: 15. For another example, human IL7 (hIL7) can contain an amino acid sequence shown as SEQ ID NO: 16.

In the present application, the term "IL21" generally refers to interleukin-21, which is secreted by activated $CD4^+$ T cells. As IL21 participates in the regulation of B cell proliferation, the loss of IL21 gene may cause the body to be more susceptible to bacteria or viruses. A study has shown that IL21 can affect the expression level of IL2 receptor protein (CD25) by regulating Bcl-6 protein. For example, mouse IL21 (mIL21) can contain an amino acid sequence shown as SEQ ID NO: 7. For another example, human IL21 (hIL21) can contain an amino acid sequence shown as SEQ ID NO: 14.

In the present application, the term "FTL3L" generally refers to a FMS-related tyrosine kinase 3 ligand, which can regulate the proliferation and differentiation of non-erythrocyte hematopoietic stem cells, promote the proliferation, differentiation and maturation of pre-B lymphocytes, dendritic cells, NK cells and cytotoxic T lymphocytes, and play an important anti-tumor role. For example, mouse FTL3L (mFTL3L) can contain an amino acid sequence shown as SEQ ID NO: 4. For another example, human FTL3L (hFTL3L) can contain an amino acid sequence shown as SEQ ID NO: 11.

In the present application, the term "GMCSF" generally refers to a granulocyte-macrophage colony stimulating factor, which can stimulate the proliferation, differentiation and activation of granulocytes and macrophages, enhance the hematopoiesis, and improve a variety of functions of neutrophils, eosinophils and mononuclear granulocytes. GMCSF can enhance the immunoactivity of immune effector cells in engulfing bacteria, killing cancer cells, etc., and can also help recover the deficiency of neutrophils due to the tumor chemotherapy and bone marrow transplantation. For example, mouse GMCSF (mGMCSF) can contain an amino acid sequence shown as SEQ ID NO: 3. For another example, human GMCSF (hGMCSF) can contain an amino acid sequence shown as SEQ ID NO: 10.

In the present application, the term "nucleic acid molecule" generally refers to an isolated nucleotide, deoxyribonucleotide or ribonucleotide of any length which is isolated from a natural environment thereof or artificially synthesized, or an analogue thereof.

In the present application, the term "vector" refers to a nucleic acid molecule capable of being self-replicated in a suitable host, which transfers the inserted nucleic acid molecules into the host cells and/or between host cells. The vector can include a vector mainly used for inserting DNA or RNA into cells, a vector mainly used for replicating DNA or RNA, and a vector mainly used for the expression of transcription and/or translation of DNA or RNA. The vector further includes a vector with a variety of the aforementioned functions. The vector can be a polynucleotide which can be transcribed and translated into a polypeptide when it is introduced into a suitable host cell. Generally, when the suitable host cells containing the vectors are cultured, these vectors can produce a desirable expression product.

In the present application, the term "cell" generally refers to a plasmid or vector which can contain or has contained the nucleic acid molecule of the present application, or individual cells, a cell line or a cell culture capable of expressing the cytokines/cytokine combinations of the present application. The cell can include the offspring of a single host cell. Due to spontaneous, accidental or deliberate mutation, the offspring cells may not be perfectly identical with the original parent cells in terms of morphology or genome, but can express the cytokines/cytokine combinations of the present application. The cell can be obtained by using the vector of the present application to transfect a cell in vitro.

In the present application, the term "pharmaceutically acceptable carrier" generally refers to one of components of a pharmaceutical composition, which can include buffer, antioxidant, preservative, low-molecular weight polypeptide, protein, hydrophilic polymer, amino acid, sugar, chelating agent, counter-ion, metal complex and/or nonionic surfactant. For example, the pharmaceutically acceptable carrier can include excipient, for example, the excipient can be selected from the group consisting of starch, dextrin, sucrose, lactose, magnesium stearate, calcium sulfate, carboxymethyl cellulose and talcum powder. For example, the pharmaceutically acceptable carrier can also be selected from the group consisting of pH regulator, osmotic pressure regulator, solubilizer and bacteriostat.

In the present application, the term "tumor" generally refers to or describes the physiological conditions of an mammal, typically characterized in the cell proliferation disorder or survival disorder. For example, the tumor can be a solid tumor, for example, selected from the group consisting of lung cancer, esophageal carcinoma, gastric carcinoma, colorectal cancer, liver cancer, breast cancer, cervical cancer, thyroid carcinoma, brain and central nervous system cancer, pancreatic cancer, oral cancer, nasopharyngeal carcinoma, head and neck cancer, laryngeal cancer, bone cancer, skin cancer, ovarian cancer, prostate cancer, testicular cancer, renal carcinoma, bladder cancer and lymphoma.

In the present application, the term "metastasis" generally refers to a process in which malignant tumor cells arrive at other site from a primary site via lymphatic channels, blood vessels or direct spreading and continue to grow. The metastasis of malignant tumor is often the main reason for the failure of tumor treatment.

In the present application, the term "recurrence" generally refers to the relapse of tumor which is induced by the residual tumor cells in the body resulting from an incomplete treatment.

In the present application, the term "about" generally refers to a variation within a range of 0.5%-10% above or below a specified value, for example, a variation within a range of 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% above or below a specified value.

Cytokine Combination

Inventors of the present application surprisingly discovered that simultaneously and topically administrating the combination of at least three cytokines selected from IL12, GMCSF, FLT3L, IL2, IL15, IL21 and IL7 to the inside of a tumor can topically activate the immune system inside the tumor, destroy the immunosuppressive microenvironment of the tumor, and motivate the immune response against the tumor, thereby effectively eliminating the tumor.

The present application provides a cytokine combination containing at least three (at least one, at least two, at least three, at least four, at least five, at least six, at least seven, at least eight, at least nine, at least ten, at least eleven, at least twelve or more) cytokines selected from the following groups: IL12 or a functional variant thereof, GMCSF or a functional variant thereof, FLT3L or a functional variant thereof, IL2 or a functional variant thereof, IL15 or a functional variant thereof, IL21 or a functional variant thereof, and IL7 or a functional variant thereof.

The cytokine combination used in the present application shows a strong synergistic effect, while the administration of a single cytokine or the combination of two cytokines cannot effectively eliminate a tumor. One of the keys of the present application is that a specific combination is designed for proteins that do not have obvious anti-tumor effects themselves, to obtain an excellent anti-tumor effect by an appropriate administration method.

Anti-tumor immune response can be activated in the body of a subject in need by administrating the cytokine combination of the present application, so that the activated immune system in the body of the subject in need can identify and eliminate tumor cells, and the acquired immune response can produce a systemic immunological memory after the tumor is eliminated. On one hand, activated tumor-specific immunocytes can circulate in the whole body via the hemic and lymphatic system, thereby suppressing and even eliminating the nidus on other sites. On the other hand, the existence of the immunological memory enables the immune system to quickly identify and kill tumor cells with similar antigens when they appear in the body once again, thereby preventing the recurrence of the tumor. In addition, as cytokine in the cytokine combination of the present application directly act on the immune system, the resistance mechanism similar to that of tumor-targeted drugs will not exist. Therefore, the cytokine combination can be repetitively applied. For example, the examples of the present application show that the tumor in the body of a mouse can be successfully eliminated by administrating the cytokine combination of the present application, and no tumor can form when the same tumor cells are inoculated into the mouse once again after a certain period of time.

In the present application, without being limited by any theory, the combination of multiple cytokines is used in the present application as different cytokines have different action mechanisms, thus simultaneously activating the innate immunity and the acquired immunity, and achieving an effective tumor treatment. For example, with a combination of three cytokines, required immune system components can be simultaneously activated to achieve the best stimulative effect for anti-tumor immunity. If a combination of less cytokines (for example, a combination only containing two cytokines) is adopted, certain components will not be activated, and as a result, the optimal therapeutic effect cannot be achieved. If a combination of more cytokines (for example, a combination of four or more cytokines) is adopt administrated, on one hand, greater side effect may be brought about, on the other hand, due to the complicated action mechanisms of the cytokines in the body, the immune system may be disordered, and consequently, a desirable immunity activation effect cannot be achieved. Therefore, in some embodiments, the cytokine combination can contain three cytokines.

For example, the cytokine combination can comprise any one of the following groups:

(1) IL12 or a functional variant thereof, GMCSF or a functional variant thereof, and IL2 or a functional variant thereof;

(2) IL12 or a functional variant thereof, GMCSF or a functional variant thereof, and IL15 or a functional variant thereof;

(3) IL12 or a functional variant thereof, GMCSF or a functional variant thereof, and IL21 or a functional variant thereof;

(4) IL12 or a functional variant thereof, FLT3L or a functional variant thereof, and IL2 or a functional variant thereof;

(5) IL12 or a functional variant thereof, FLT3L or a functional variant thereof, and IL15 or a functional variant thereof;

(6) IL12 or a functional variant thereof, FLT3L or a functional variant thereof, and IL21 or a functional variant thereof;

(7) IL12 or a functional variant thereof, GMCSF or a functional variant thereof, and IL7 or a functional variant thereof; and (8) IL12 or a functional variant thereof, FLT3L or a functional variant thereof, and IL7 or a functional variant thereof.

In the present application, mouse IL2 (mIL2) can contain an amino acid sequence shown as SEQ ID NO: 5, and human cytokine IL2 (hIL2) can contain an amino acid sequence shown as SEQ ID NO: 12. In the present application, the p35 subunit in mouse IL12 (mIL12) can contain an amino acid sequence shown as SEQ ID NO: 1, and the p40 subunit can contain an amino acid sequence shown as SEQ ID NO: 2; the p35 subunit in human IL12 (hIL12) can contain an amino acid sequence shown as SEQ ID NO: 8, and the p40 subunit can contain an amino acid sequence shown as SEQ ID NO: 9. In the present application, mouse IL15 (mIL15) can contain an amino acid sequence shown as SEQ ID NO: 6, and human IL15 (hIL15) can contain an amino acid sequence shown as SEQ ID NO: 13. In the present application, mouse IL21 (mIL21) can contain an amino acid sequence shown as SEQ ID NO: 7, and human IL21 (hIL21) can contain an amino acid sequence shown as SEQ ID NO: 14. In the present application, mouse FTL3L (mFTL3L) can contain an amino acid sequence shown as SEQ ID NO: 4, and human FTL3L (hFTL3L) can contain an amino acid sequence shown as SEQ ID NO: 11. In the present application, mouse GMCSF (mGMCSF) can contain an amino acid sequence shown as SEQ ID NO: 3, and human GMCSF (hGMCSF) can contain an amino acid sequence shown as SEQ ID NO: 10. In the present application, mouse IL7 (mIL7) can contain an amino acid sequence shown as SEQ ID NO: 15, and human IL7 (hIL7) can contain an amino acid sequence shown as SEQ ID NO: 16. In some embodiments, the functional variant can be an amino acid sequence that has substantially the same functions as the cytokine (such as IL2, IL12, IL15, IL21, FTL3L, GMCSF or IL7) and has at least about more than 80% (such as at least about more than 80%, about more than 85%, about more than 90%, about more than 91%, about more than 92%, about more than 93%, about more than 94%, about more than 95%, about more than 96%, about more than 97%, about more than 98%, about more than 99%, or more) of homology with that cytokine. In some embodiments, the functional variant is an amino acid sequence that has substantially the same functions as the cytokine (such as IL2, IL12, IL15, IL21, FTL3L, GMCSF or IL7) and involves the addition, deletion or substitution of one or more (such as 1 to 2, 1 to 3, 1 to 4, 1 to 5, 1 to 6, 1 to 7, 1 to 8, 1 to 9, 1 to 10, or more) amino acids on the basis of that cytokine.

In the present application, the cytokines are mammal cytokines, such as mouse cytokines or human cytokines.

In the present application, the concentration of each cytokine in the cytokine combination can be 1-10000 ng/μL (such as 1-100000 ng/μL, 1-10000 ng/μL, 2-10000 ng/μL, 4-10000 ng/μL, 6-10000 ng/μL, 8-10000 ng/μL, 10-10000 ng/μL, 10-1000 ng/μL, 100-1000 ng/μL or 10-500 ng/μL).

In the present application, the proportion of each cytokine in the cytokine combination can be any proportion, as long as the dose of each cytokine is a therapeutically effective amount respectively. For example, the proportion of three different cytokines in the cytokine combination can be x:y:z, wherein x, y and z are independently selected from integers of 1 to 10 (for example, x, y and z are independently selected from integers of 1 to 2, 1 to 3, 1 to 4, 1 to 5, 1 to 6, 1 to 7, 1 to 8, 1 to 9 or 1 to 10). In some embodiments, the proportion of three different cytokines in the cytokine combination can be 5:1:1, 1:5:1, 1:1:5, 4:1:1, 1:4:1, 1:1:4, 3:1:1, 1:3:1, 1:1:3, 2:1:1, 1:2:1, 1:1:2 or 1:1:1. For example, the proportion of three different cytokines in the cytokine combination can be 1:1:1.

In the present application, each cytokine in the cytokine combination can be simultaneously administrated with others or separately administrated within an appropriate time interval (for example, the third cytokine can be administrated within 0.5 to 5 days, 1 to 4 days, 1 to 3 days, 1 to 2 days, 11 to 24 hrs, 10 to 24 hrs, 9 to 24 hrs, 8 to 24 hrs, 7 to 24 hrs, 6 to 24 hrs, 5 to 24 hrs, 4 to 24 hrs, 3 to 24 hrs, 2 to 24 hrs, 1 to 24 hrs, 55 to 60 min, 50 to 60 min, 45 to 60 min, 40 to 60 min, 35 to 60 min, 30 to 60 min, 25 to 60 min, 20 to 60 min, 15 to 60 min, 10 to 60 min, 5 to 60 min, 4 to 60 min, 3 to 60 min, 2 to 60 min, 1 to 60 min, 0.5 to 60 min or other time intervals after the administration of the first and/or the second cytokine). For example, each cytokine can be simultaneously administrated with others.

The cytokine contained in the cytokine combination of the present application has strong capabilities of activating the immune system to resist tumors, and has been clinically applied for years. However, just because of the powerful functions of these cytokines, the whole body use of a small dose administrated can bring about severe side effects, and can hardly achieve a therapeutically-effective and sufficient action concentration in local tumor administrated. In the present application, the effect of topical enrichment in a tumor of the cytokine in the cytokine combination can be achieved though a direct administration at the tumor site, thereby avoiding the systemic side effects administration. The present application have verified through experiments that the mouse intratumorally injected with the cytokine combination of the present application showed no special abnormal response, which demonstrates that the cytokine combination of the present application will not bring severe side effects to a subject in need. In some embodiments, the cytokine combination can be prepared to be suitable for topical administration. For example, the cytokine combination can be prepared for intratumoral administration.

In the present application, the cytokine combination can be prepared for slow-release administration. This is because these cytokines can't stay in a tumor for a long time but are rapidly brought away by the circulating system if they are injected into the tumor only with water or normal saline as a carrier, severely affecting their performance. In the present application, the cytokine can be enriched in the administration site for a long time by a slow-release technique, thus obtaining a longer retention and action time. For example, slow-release can be achieved by controlling the dissolution speed of the cytokine, controlling the diffusion speed of the cytokine, utilizing corrosion or permeation, or adopting ion exchange. For example, the cytokine in the cytokine combination can be prepared into polylactic acid (PLA) microspheres or calcium alginate gel, or the viscosity of the cytokine solution can be increased by adding chitosan quaternary ammonium salt, so that the cytokine can be retained at an injection site for a long time. Other slow-release techniques known in the art, such as polylactic-co-glycolic acid (PLGA) microspheres, slow-release microspheres of temozolomide, block copolymer micelles, a slow-release pump, etc., can be applied to the cytokine combination.

The cytokine combination of the present application can be administrated into a tumor by any appropriate means. For example, the cytokine combination can be directly injected into a tumor site. Or, the intravenously-administrated cytokine can be enriched in the tumor site by being coupled with a tumor-targeted substance (such as an antibody).

Nucleic Acid, Vector and Cell

The present application provides a nucleic acid, i.e., one or more nucleic acid molecules, which encode the cytokine combination.

In some embodiments, the nucleic acid molecule includes more than two (such as more than one, more than two, more than three, more than four, or more) nucleic acid molecule, wherein, each of the nucleic acid molecule encodes one or more (such as more than one, more than two, more than three, more than four, or more) cytokines, and each of the nucleic acid molecule encodes the cytokine which is different from the a cytokine encoded by at least one of the other nucleic acid molecule.

The nucleic acid molecule of the present application can be isolated. For example, the nucleic acid molecule can be produced or synthesized by the following methods: (1) in-vitro amplification, such as polymerase chain reaction (PCR) amplification; (2) cloning and recombination; (3) purification, such as digestion and gel electrophoresis separation; (4) synthesis, such as chemical synthesis. In some embodiments, the isolated nucleic acid is nucleic acid molecule prepared by the recombinant DNA technology.

In the present application, the nucleic acid for encoding the antibody, the antigen-binding fragment or a variant thereof can be prepared by a variety of methods known in the art, including but not limited to adopting restriction fragment operation or SOE PCR of synthesized oligonucleotide, and for specific operations, see Sambrook, et al, Molecular Cloning, A Laboratory Manual, Cold Spring Harbor Laboratory Press, Cold Spring Harbor, N.Y., 1989; and Ausube, et al, Current Protocols in Molecular Biology, Greene Publishing and Wiley-Interscience, New York N.Y., 1993.

The present application provides a vector containing the nucleic acid molecule.

In some embodiments, the vector include more than two (such as more than one, more than two, more than three, more than four, or more) vectors, wherein, each of the vector contains one or more (such as more than one, more than two, more than three, more than four or more) nucleic acid molecules, and the cytokine encoded by the nucleic acid molecule contained in each of the vector is different from the cytokine encoded by the nucleic acid molecule contained in at least one of the other vector.

In the present application, the vector can be linear nucleic acid fragment, circular plasmid or viral vector (such as vaccinia virus, adenovirus, adeno-associated virus, lentivirus, etc.). In the vector, nucleotide sequence encoding the cytokine can be operatively linked to expression regulatory sequence. The terms "regulatory sequence" and "regulatory element" can be used interchangeably, and can refer to nucleotide sequence which is located upstream (5' noncoding sequences), in the middle or downstream (3' noncoding sequences) of coding sequence and influence the transcription of related coding sequence and the processing, stability or translation of RNA. The regulatory sequence can include but is not limited to promoter, translation leader sequence, intron and polyadenylation recognition sequence. The term "operably linked" refers to that the regulatory element (such as, but not limited to, promoter sequence, transcription termination sequence, etc.) can be linked to nucleic acid sequence (such as coding sequence or open reading frame) so that the transcription of the nucleotide sequence is controlled and regulated by the transcription regulatory element. The technique for operatively linking the regulatory element region to the nucleic acid molecule is known in the art.

The present application further provides a cell capable of being administrated to a tumor site. The cell contain the nucleic acid molecule or the vector.

In some embodiments, the cell include more than two (such as more than one, more than two, more than three, more than four, or more) cells, wherein, each of the cell expresses one or more (such as more than one, more than two, more than three, more than four, or more) cytokines, and the cytokine encoded by each of the cell is different from the cytokine expressed by at least one of the other cell. For example, in the case of the cytokine combination containing three cytokines, the cell can express all the three cytokines (A, B and C); or the cell can include two cells, one of the cell expresses one cytokine (A or B or C), and the other cell expresses the other two cytokines (B and C; or A and C; or A and B); or the cell can include three cells, and each of the cell expresses one unique cytokine respectively.

In the present application, the cell can continuously express the cytokine of the present application at a tumor site, so that a certain concentration of the cytokine can be maintained inside the tumor for a long time, thereby exerting an anti-tumor effect.

In the present application, methods for introducing the vector into the cell include but are not limited to calcium phosphate transfection, protoplast fusion, electroporation, lipofection, microinjection and viral infection.

In the present application, the cell can be eukaryocyte, such as mammal cell. The mammal can be selected from the group consisting of human being, mouse, rat, monkey, dog, pig, sheep, cow and cat. For example, the mammal can be human being. For example, the cell can be the 293 cell line.

The present application further provides a method for preparing the cytokine combination/cytokine. The method can include culturing the cell under the condition of enabling the cytokine combination/cytokine to be expressed. For example, via an appropriate medium, an appropriate temperature and culture time, etc., and these methods are known by those of ordinary skill in the art.

Pharmaceutical Composition and Application

The present application provides a pharmaceutical composition, containing the cytokine combination, the nucleic acid molecule, the vector or the cell, and optionally a pharmaceutically acceptable carrier.

The pharmaceutically acceptable adjuvant can include solvent, dispersion medium, coating, antibacterial agent, antifungal agent, antioxidant, isotonic agent, absorption retarder and excipient. For example, the pharmaceutically acceptable adjuvant can include buffer, antioxidant, preservative, low-molecular weight polypeptide, protein, hydrophilic polymer, amino acid, sugar, chelating agent, counterion, metal complex and/or nonionic surfactant.

In the present application, the pharmaceutical composition can be prepared to be administrated orally, intravenously, intramuscularly, rectally, vaginally or transdermally, or to be administrated in situ in a tumor site, by inhalation, or via a subcutaneous reservoir.

In some embodiments, the pharmaceutical composition is prepared to be suitable for topical administration, such as intratumoral administration.

In some embodiments, the pharmaceutical composition is prepared to be suitable for slow-release administration. For example, the pharmaceutical composition is prepared in a calcium alginate gel, a polylactic acid microsphere or a chitosan quaternary ammonium salt solution.

The pharmaceutical composition can be used to suppress the tumor growth. For example, the pharmaceutical composition of the present application can inhibit or retard the development or progression of a disease, reduce a tumor size (even substantially eliminate a tumor), and/or alleviate and/or stabilize the disease condition.

The pharmaceutical composition of the present application can contain a therapeutically effective amount of the cytokine combination. The therapeutically effective amount is a dose required to prevent and/or treat (at least partially treat) a disease (such as cancer) and/or any complication thereof in a subject having that disease or the development risk therefor. Wherein, the "effective amount" can refer to the dose of the administrated pharmaceutical composition required to suppress the proliferation of tumor cell or the increase of the tumor area by at least about 10% (such as at least about 10%, 20%, 30%, 40%, 50%, 60%, 70%, 80%, 90%, 99% or 100%) compared with the case where the pharmaceutical composition is not administrated. Wherein, the capability for suppressing the increase of the tumor area can be evaluated by an animal model related to that tumor, or can also be evaluated by examining the capability for suppressing the cell growth.

The pharmaceutical composition of the present application can remarkably decrease the severity of a disease, increase the frequency of an asymptomatic period for a disease, prolong the duration of an asymptomatic period for a disease, prevent and treat injuries or disability caused by a disease, and/or prevent or treat the metastasis or recurrence of a tumor.

When administrated, the dose of the pharmaceutical composition can be about 0.0001-100 mg per kg of the body weight of a subject in need (such as 0.0001-100 mg/kg, 0.01-100 mg/kg, 0.05-100 mg/kg, 0.1-100 mg/kg, 0.5-100 mg/kg, 1-100 mg/kg, 5-100 mg/kg or 0.01-20 mg/kg).

In the present application, the dosage regimen of the pharmaceutical composition can be that the pharmaceutical composition is administrated once a week, once every two weeks, once every three weeks, once every four weeks, once a month, once every three months, or once every three to six months, or administrated at a slightly short interval (such as once a week to once every three weeks) at the beginning and at a longer interval (such as once a month to once every three to six months) later. The specific dosage regimen is determined according to the disease progression of a subject in need. For example, it can be started to deliver the pharmaceutical composition to a mouse when the tumor area of the mouse reaches a certain threshold value.

The present application provides a method for treating tumor and/or preventing the recurrence or metastasis of tumor, which includes administrating the cytokine combination, the nucleic acid molecule, the vector, the cell or the pharmaceutical composition to a subject in need.

The present application provides an application of the cytokine combination, the nucleic acid molecule, the vector, the cell or the pharmaceutical composition in treating tumor and/or preventing the recurrence or metastasis of tumor.

The present application further provides an application of the cytokine combination, the nucleic acid molecule, the vector, the cell or the pharmaceutical composition in the preparation of drug which are used to treat tumor and/or prevent the recurrence or metastasis of tumor.

In the present application, the tumor may be solid tumor. For example, the tumor can be selected from the group consisting of lung cancer, esophageal carcinoma, gastric carcinoma, colorectal cancer, liver cancer, breast cancer, cervical cancer, thyroid carcinoma, brain and central nervous system cancer, pancreatic cancer, oral cancer, nasopharyngeal carcinoma, head and neck cancer, laryngeal cancer, bone cancer, skin cancer, ovarian cancer, prostate cancer, testicular cancer, renal carcinoma, bladder cancer, eyelid neoplasm, leukemia and lymphoma.

In the pharmaceutical composition and/or method of the present application, the concentration of each cytokine can be 1-10000 ng/μL (such as 1-100000 ng/μL, 1-10000 ng/μL, 2-10000 ng/μL, 4-10000 ng/μL, 6-10000 ng/μL, 8-10000 ng/μL, 10-10000 ng/μL, 10-1000 ng/μL, 10-500 ng/μL or 1-100 ng/μL).

The administration can be topical administration, such as intratumoral administration. The administration can be single administration or multiple administrations. For example, they can be administrated twice a week, once a week, once every two weeks, once every three weeks, once every four weeks, once a month, once every three months, or once every three to six months, or administrated at a slightly short interval (such as once a week to once every three weeks) at the beginning and at a longer interval (such as once a month to once every three to six months) later.

In the present application, the subject is mammal. For example, the mammal is selected from the group consisting of human being, mouse, rat, monkey, dog, pig, sheep, cow and cat. For another example, the subject are human being.

Without intending to be bound by any theory, the examples hereinafter are merely intended to illustrate the working modes of the device, method and system of the present application, rather than to limit the scope of the invention of the present application.

EXAMPLES

The present application will be further described in detail below by reference to the examples, but the scope for which the present application claims protection is not limited to the scope of the examples.

Reagents: DMEM medium, 1640 medium and fetal bovine serum were purchased from Life Technologies; cell culture flasks and culture plates were purchased from Corning; Puromycin was purchased from Life Technologies; restriction endonuclease was purchased from Takara and NEB; T4 DNA ligase was purchased from NEB; DNA polymerase was purchased from Takara; plasmid extraction kits and gel extraction kits were purchased from Omega Biotech; and primer synthesis, gene synthesis and sequencing were performed by Life Technologies. Sodium alginate, calcium chloride, BSA, petroleum ether, methylene chloride, polylactic acid (molecular weight: 20000) and polylactic acid (molecular weight: 5000) were purchased from Sigma-Aldrich; and chitosan quaternary ammonium salt was purchased from Zhejiang Golden-Shell Pharmaceutical Co., Ltd.

mIL12, mGMCSF, mFLT3L, mIL2, mIL15, mIL21 and mIL7 represent mouse IL12, mouse GMCSF, mouse FLT3L, mouse IL2, mouse IL15, mouse IL21 and mouse IL7 respectively. hIL12, hGMCSF, hFLT3L, hIL2, hIL15, hIL21 and hIL7 represent human IL12, human GMCSF, human FLT3L, human IL2, human IL15, human IL21 and human IL7 respectively. The aforementioned cytokines were purchased from Peprotech.

6-to-8-week-old female C57BL/6 and Balb/c mice were purchased from Beijing Huafukang Biotechnology Co., Ltd.

In FIGS. 1-20 and 22-31, each broken line represents the tumor area state in the body of one mouse.

Example 1

The Therapeutic Effect of the mIL12+mGMCSF+mIL2 Chitosan Quaternary Ammonium Salt Solution on the Mouse Melanoma The cultured mouse melanoma cells (B16F10) were digested, and $2*10^5$ of these cells were subcutaneously injected into the right side of the body of a C57BL/6 mouse. The treatment was started when the long diameter of a tumor reached about 7-9 mm.

The cytokines mIL12, mGMCSF and mIL2 were dissolved in sterile water respectively so that each had a final concentration of 200 ng/μl. 15 μl of each of these cytokine aqueous solutions was taken and mixed to obtain 45 μl μl of the mIL12+mGMCSF+mIL2 mixture solution, then 45 μl of 3% chitosan quaternary ammonium salt solution prepared in advance was added, and the final solution was carefully pipetted for blending. Pentobarbital sodium was injected into the abdominal cavities of the tumor-bearing mice for anesthesia, then a 29G insulin syringe was used to extract and slowly inject the prepared cytokine chitosan quaternary ammonium salt solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

The experimental results are shown in FIG. 1. All mice receiving injection showed regression in tumors. However, tumors recurred at the original tumor sites in 60% of the mice about one to two weeks after tumor regression. When the recurring tumors grew to 6-8 mm, the mIL12+mGMCSF+mIL2 chitosan quaternary ammonium salt solutions were injected once again by the same method, then all tumors regressed completely.

Example 2

The Therapeutic Effect of the mIL12+mGMCSF+mIL2 Chitosan Quaternary Ammonium Salt Solution on the Mouse Colon Cancer The cultured mouse colon cancer cells (CT26) were digested, and $5*10^5$ of these cells were subcutaneously injected into the right side of the body of a Balb/c mouse. The treatment was started when the long diameter of a tumor reached about 7-9 mm.

The cytokines mIL12, mGMCSF and mIL2 were dissolved in sterile water respectively so that each had a final concentration of 200 ng/µl. 15 µl of each of these cytokine aqueous solutions was taken and mixed to obtain 45 µl of the mIL12+mGMCSF+mIL2 mixture solution, then 45 µl of 3% chitosan quaternary ammonium salt solution prepared in advance was added, and the final solution was carefully pipetted for blending. Pentobarbital sodium was injected into the abdominal cavities of the tumor-bearing mice for anesthesia, then a 29G insulin syringe was used to extract and slowly inject the prepared cytokine chitosan quaternary ammonium salt solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

Figure 2:
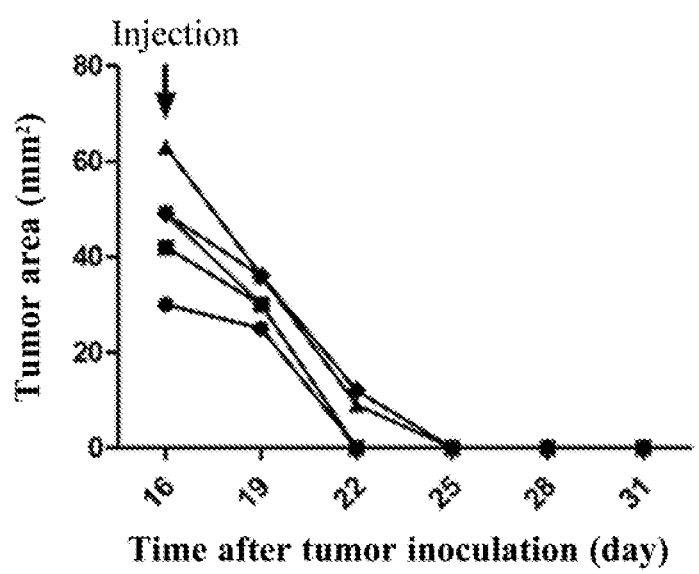
FIG. 2 shows the therapeutic effect of the mIL12+mGMCSF+mIL2 chitosan quaternary ammonium salt solution on the mouse colon cancer (CT26).

The experimental results are shown in FIG. 2. Tumors of all the mice receiving injection regressed completely.

Example 3

The Therapeutic Effect of the mIL12+mGMCSF+mIL2 Chitosan Quaternary Ammonium Salt Solution on the Mouse Breast Cancer The cultured mouse breast cancer cells (4T1) were digested, and $2*10^5$ of these cells were subcutaneously injected into the right side of the body of a Balb/c mouse. The treatment was started when the long diameter of a tumor reached about 7-9 mm.

The cytokines mIL12, mGMCSF and mIL2 were dissolved in sterile water respectively so that each had a final concentration of 200 ng/µl. 15 µl of each of these cytokine aqueous solutions was taken and mixed to obtain 45 µl of the mIL12+mGMCSF+mIL2 mixture solution, then 45 µl of 3% chitosan quaternary ammonium salt solution prepared in advance was added, and the final solution was carefully pipetted for blending. Pentobarbital sodium was injected into the abdominal cavities of the tumor-bearing mice for anesthesia, then a 29G insulin syringe was used to extract and slowly inject the prepared cytokine chitosan quaternary ammonium salt solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

Figure 3:
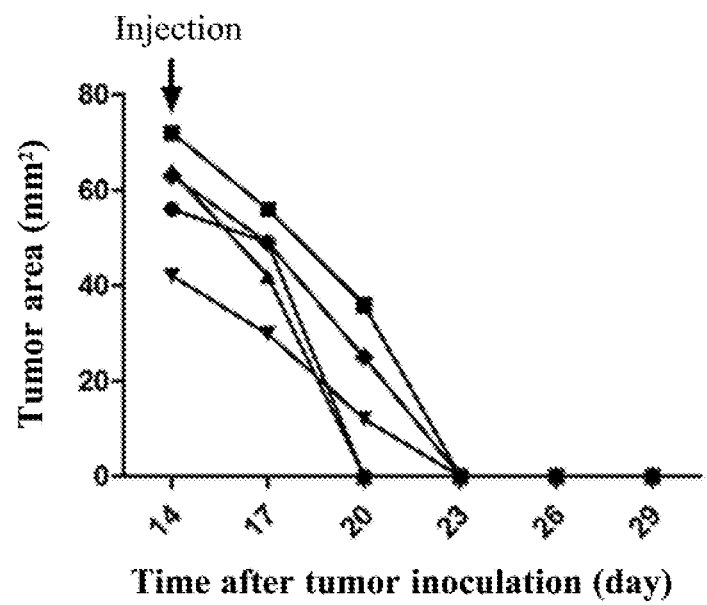
FIG. 3 shows the therapeutic effect of the mIL12+mGMCSF+mIL2 chitosan quaternary ammonium salt solution on the mouse breast cancer (4T1).

The experimental results are shown in FIG. 3. Tumors of all the mice receiving injection regressed completely.

Example 4

The Therapeutic Effect of the mIL12+mGMCSF+mIL2 Chitosan Quaternary Ammonium Salt Solution on the Mouse Lymphoma The cultured mouse lymphoma cells (EL4) were digested, and $2*10^6$ of these cells were subcutaneously injected into the right side of the body of a C57BL/6 mouse. The treatment was started when the long diameter of a tumor reached about 7-9 mm.

The cytokines mIL12, mGMCSF and mIL2 were dissolved in sterile water respectively so that each had a final concentration of 200 ng/µl. 15 µl of each of these cytokine aqueous solutions was taken and mixed to obtain 45 µl of the mIL12+mGMCSF+mIL2 mixture solution, then 45 µl of 3% chitosan quaternary ammonium salt solution prepared in advance was added, and the final solution was carefully pipetted for blending. Pentobarbital sodium was injected into the abdominal cavities of the tumor-bearing mice for anesthesia, then a 29G insulin syringe was used to extract and slowly inject the prepared cytokine chitosan quaternary ammonium salt solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

Figure 4:
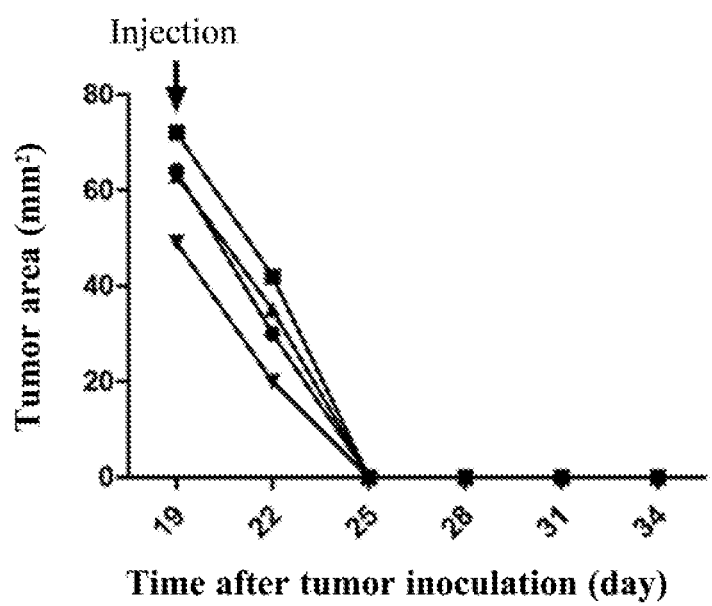
FIG. 4 shows the therapeutic effect of the mIL12+mGMCSF+mIL2 chitosan quaternary ammonium salt solution on the mouse lymphoma (EL4).

The experimental results are shown in FIG. 4. Tumors of all the mice receiving injection regressed completely.

Example 5

The Therapeutic Effects of mIL12+mGMCSF+mIL2 Chitosan Quaternary Ammonium Salt Solutions in Different Proportions on the Mouse Breast Cancer The cultured mouse breast cancer cells (4T1) were digested, and $2*10^5$ of these cells were subcutaneously injected into the right side of the body of a Balb/c mouse. The treatment was started when the long diameter of a tumor reached about 7-9 mm.

The cytokines mIL12, mGMCSF and mIL2 were dissolved in sterile water respectively so that a solution of 200 ng/µl and a solution of 1000 ng/µl were prepared for each of the cytokines. 15 µl of mIL12 (1000 ng/µl), 15 µl of mGMCSF (200 ng/µl) and 15 µl of mIL2 (200 ng/µl) were taken and mixed to obtain 45 µl of mIL12+mGMCSF+mIL2 (5:1:1) mixture solution, then 45 µl of 3% chitosan quaternary ammonium salt solution prepared in advance was added, and the final solution was carefully pipetted for blending.

15 µl of mIL12 (200 ng/µl), 15 µl of mGMCSF (1000 ng/µl) and 15 µl of mIL2 (200 ng/µl) were taken and mixed to obtain 45 µl of mIL12+mGMCSF+mIL2 (1:5:1) mixture solution, then 45 µl of 3% chitosan quaternary ammonium salt solution prepared in advance was added, and the final solution was carefully pipetted for blending.

15 µl of mIL12 (200 ng/µl), 15 µl of mGMCSF (200 ng/µl) and 15 µl of mIL2 (1000 ng/µl) were taken and mixed to obtain 45 µl of mIL12+mGMCSF+mIL2 (1:1:5) mixture solution, then 45 µl of 3% chitosan quaternary ammonium salt solution prepared in advance was added, and the final solution was carefully pipetted for blending.

Pentobarbital sodium was injected into the abdominal cavities of the tumor-bearing mice for anesthesia, then a 29G insulin syringe was used to extract and slowly inject the prepared cytokine chitosan quaternary ammonium salt solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

Figure 5:
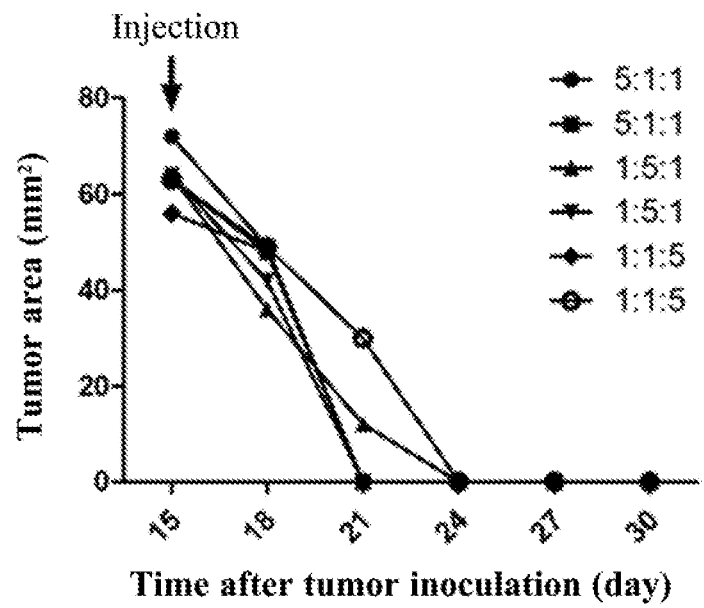
FIG. 5 shows the therapeutic effects of the mIL12+mGMCSF+mIL2 chitosan quaternary ammonium salt solutions in different proportions on the mouse breast cancer (4T1).

The experimental results are shown in FIG. 5. Tumors of all the mice receiving injection regressed completely, which indicated that a good and enough anti-tumor effect could also be achieved by adopting the cytokine combinations containing cytokines with different proportions.

Example 6

The Therapeutic Effect of the mIL12+mGMCSF+mIL2 Calcium Alginate Gel on the Mouse Breast Cancer The cultured mouse breast cancer cells (4T1) were digested, and 2*10⁵ of these cells were subcutaneously injected into the right side of the body of a Balb/c mouse. The treatment was started when the long diameter of a tumor reached about 7-9 mm.

The cytokines mIL12, mGMCSF and mIL2 were dissolved in sterile water respectively so that each had a final concentration of 200 ng/µl. 15 µl of each of these cytokine aqueous solutions was taken and mixed to obtain 45 µl of mIL12+mGMCSF+mIL2 mixture solution, then 1.5 µl of 2 M calcium chloride solution was added, and the mixture solution was mixed. Finally, 45 µl of 1% sodium alginate was added, and the final solution was pipetted for blending, then the gel was formed. Pentobarbital sodium was injected into the abdominal cavities of the tumor-bearing mice for anesthesia, then a 29G insulin syringe was used to extract and slowly inject the prepared cytokine calcium alginate gel into the tumor. After the injection was completed, the syringe needle was detained therein for a short time to reduce the overflow of the solution. The rejected mice were put back into the cage, and kept warm until they woke up. The growth of the tumors in the mice was observed and recorded.

Figure 6:
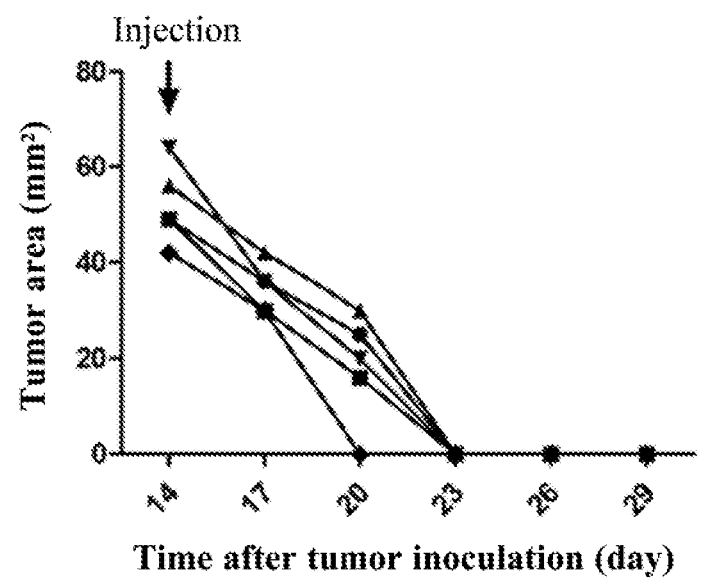
FIG. 6 shows the therapeutic effect of the mIL12+mGMCSF+mIL2 calcium alginate gel on the mouse breast cancer (4T1).

The experimental results are shown in FIG. 6. Tumors of all the mice receiving injection regressed completely.

Example 7

The Therapeutic Effect of mIL12+mGMCSF+mIL2 Polylactic Acid Microspheres on the Mouse Breast Cancer The cultured mouse breast cancer cells (4T1) were digested, and 2*10⁵ of these cells were subcutaneously injected into the right side of the body of a Balb/c mouse. The treatment was started when the long diameter of a tumor reached about 7-9 mm.

2 mg of polylactic acid (the proportion of molecular weight 20000 to molecular weight 5000 therein is 1:1), 0.02 mg of BSA and 30 µg of cytokine (mIL12, or mGMCSF or mIL2) were taken and added to dichloromethane, and the mixture solution was mixed and then quickly poured into petroleum ether so that microspheres were formed. Then the solution was sucked away, and the residue was lyophilized to obtain polylactic acid microspheres coated with the cytokine. For administration, 0.3 mg of mIL12 microspheres, 0.3 mg of mGMCSF microspheres and 0.3 mg of mIL2 microspheres were mixed and resuspended in 100 µl of DMEM, and a 28G syringe was used to slowly inject the well-mixed solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

Figure 7:
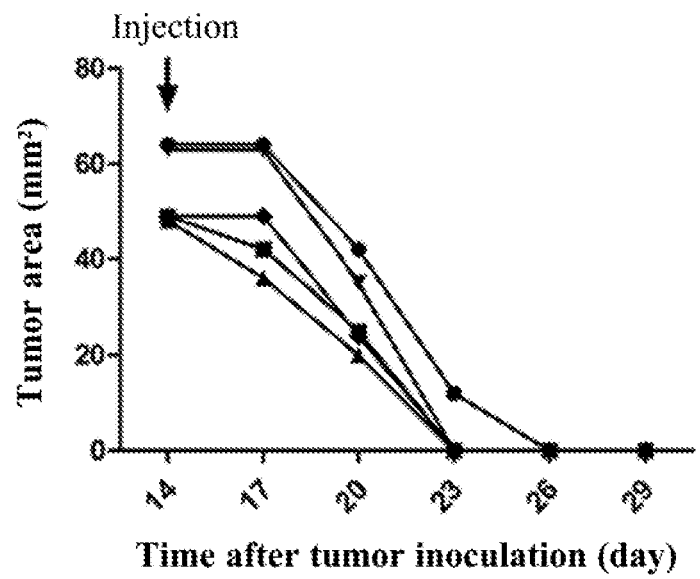
FIG. 7 shows the therapeutic effect of mIL12+mGMCSF+mIL2 polylactic acid microspheres on the mouse breast cancer (4T1).

The experimental results are shown in FIG. 7. Tumors of all the mice receiving injection regressed completely.

Example 8

The Therapeutic Effect of Cell Expressing mIL12+mGMCSF+mIL2 on the Mouse Breast Cancer The vector pLentis-CMV-MCS-IRES-PURO was digested in a EP tube, and the digestion system was as follows: 2 µg of plasmid, 3 µl of digestion buffer, 1 µl of BamHI, 1 µl of XhoI, water with an amount resulting in a total volume of 30 µl, and 12 hrs of standing at 37° C. Take out the EP tube, 3.3 µl of 10*loading buffer was added to the EP tube, and electrophoresis was performed on the solution with 1% agarose gel. After the electrophoresis was completed, vector fragments were recovered for later use.

DNA sequences corresponding to mIL12, mGMCSF and mIL2 gene coding regions were synthesized respectively, and a BamHI digestion site was added to the 5' end thereof and an XhoI digestion site was added to the 3' end thereof during the synthesis process. Synthesized plasmids with target genes were digested, and the reaction system was as follows: 5 µg of plasmid, 4 µl of digestion buffer, 1 µl of BamHI, 1 µl of XhoI, water with an amount resulting in a total volume of 40 µl, and 12 hrs of standing at 37° C. Take out the EP tube, 4.4 µl of 10*loading buffer was added to the EP tube, and electrophoresis was performed on the solution with 1% agarose gel. After the electrophoresis was completed, mIL12, mGMCSF and mIL2 fragments were recovered for later use.

pLentis-CMV-MCS-IRES-PURO was linked to mIL12, mGMCSF and mIL2, and the reaction system was as follows: 2 µl of pLentis-CMV-MCS-IRES-PURO, 2 µl of mIL12, mGMCSF or mIL2, 1 µl of ligase buffer, 0.5 µl of T4 DNA ligase, and 4.5 µl of water. The reaction solution was placed at room temperature for 4 hrs. The linking system then underwent the transformation of *Escherichia coli* competence. On the next day, colonies were picked from the transformed plate and cultured overnight in LB medium in a vibrator at 37° C. The plasmid extraction kit was used to extract plasmids from the cultured bacteria, and whether the fragments were linked to the vectors was determined by digestion. The correct vectors were then sequenced to determine that the construction was successful. Viral vectors pLentis-CMV-mIL12-IRES-PURO, pLentis-CMV-mGMCSF-IRES-PURO and pLentis-CMV-mIL2-IRES-PURO which express mIL12, mGMCSF and mIL2 were obtained.

The virus expressing a vector was prepared, and the method was as follows: (1) the cultured 293FT cells were digested, then inoculated into a 10-cm culture dish with 3*10⁶ cells/well after the cell counting, and the volume of the culture solution is 10 ml in each of the total five dishes; (2) in the night of the next day, the state of the cells was observed, and if the state of the cells was good, transfection was conducted; chloroquine was added to the culture dish so that the solution had a final concentration of 25 µM, then sterile water and plasmid (pMD2.G 6 µg+pSPAX2 15 µg+pLentis-CMV-mIL12-IRES-PURO or pLentis-CMV-mGMCSF-IRES-PURO or pLentis-CMV-mIL2-IRES-PURO 20 µg) were added to a test tube, with a total volume of 1045 µl, and 155 µl of 2 M CaCl₂ was added, and finally, 1200 µl of 2*HBS was added dropwise under shaking, after the adding of 1200 µl of 2*HBS, then the resultant solution was rapidly added into cell culturing wells which was then gently shaken for blending; (3) in the morning of the third day, the state of the cells was observed, and the medium was replaced with 10 ml of fresh DMEM medium; (4) in the morning of the fifth day, the state of the cells was observed, and the supernate in the culture dish was collected and filtered with a 0.45 μm filter, then the filtrate was put into a high-speed centrifuge tube and centrifuged at 50000 g for 2 hrs, and the resultant supernate was carefully removed, then the residue was dried to a maximum degree with absorbent papers, and suspended in 200 μl of HBSS, and after 2 hrs of dissolution, the solution was loaded into small tubes and stored at −70° C.

The expression virus was used to transfect 293A cells, and the method was as follows: the cultured 293A cells were digested and inoculated into a 6-well plate with $10^5$ cells/well, and the volume of the culture solution was 1 ml; 24 hrs later, 10 μl of expression virus solution was added; after the culture was continuously cultured for 24 hrs in an incubator, the supernate was replaced with fresh medium for the continuous culture of the cells; after the cells' confluence reached 100%, the cells were transferred into a culture flask and added with puromycin (final concentration: 3 μg/ml), and the cells were continuously cultured, wherein the medium was replaced once every two days, and the concentration of puromycin was kept at that concentration; and after one week of screening, the surviving cells were the ones which can stably express the cytokines, and that were 293A (mIL12), 293A (mGMCSF) and 293A (mIL2) respectively.

The cultured mouse breast cancer cells (4T1) were digested, and $2*10^5$ of these cells were subcutaneously injected into the right side of the body of a Balb/c mouse. The treatment was started when the long diameter of a tumor reached about 7-9 mm.

The cultured 293A (mIL12), 293A (mGMCSF) and 293A (mIL2) cells were digested, collected by centrifugation, washed with medium, and then the suspension was centrifuged again. The cells were suspended with medium to a concentration of $2*10^7$ cells/ml, 15 μl of suspension for each of the three cells was taken and mixed to obtain 45 μl of mixture solution, then 1.5 μl of 2 M calcium chloride solution was added, and the mixture solution was mixed. Finally, 45 μl of 1% sodium alginate was added, and the final solution was pipetted for blending, then the gel was formed. Pentobarbital sodium was injected into the abdominal cavities of the tumor-bearing mice for anesthesia, then a 29G insulin syringe was used to extract and slowly inject the calcium alginate gel with cytokine-expressed cells into the tumor. After the injection was completed, the syringe needle was detained therein for a short time to reduce the overflow of the solution. The rejected mice were put back into the cage, and kept warm until they woke up. The same injection operation was performed once again for the tumors which did not regress on the 6th day after the first injection. The growth of the tumors in the mice was observed and recorded.

Figure 8:
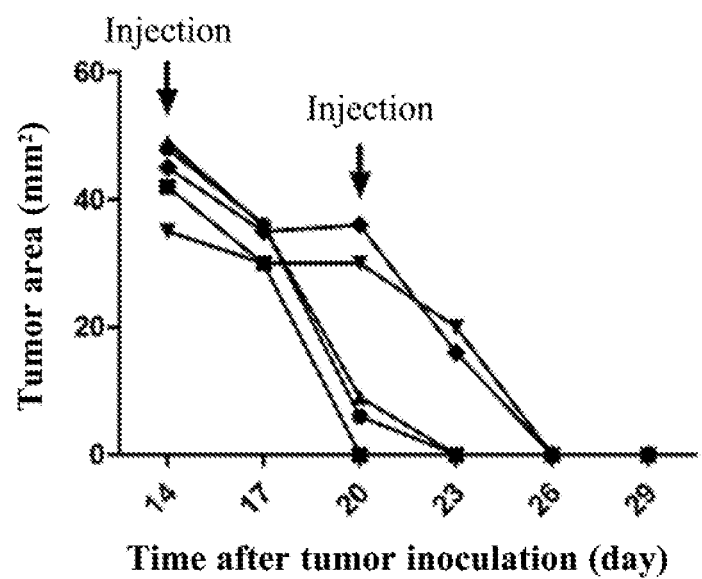
FIG. 8 shows the therapeutic effect of the cell expressing mIL12+mGMCSF+mIL2 on the mouse breast cancer (4T1).

The experimental results are shown in FIG. 8. Tumors of 60% of the mice receiving injection regressed completely after a first injection, and the rest 40% of the mice received a second injection six days after the first injection, then tumors of all the mice regressed completely after the second injection.

Example 9

The Therapeutic Effect of the mIL12+mGMCSF+mIL15 Chitosan Quaternary Ammonium Salt Solution on the Mouse Breast Cancer The cultured mouse breast cancer cells (4T1) were digested, and $2*10^5$ of these cells were subcutaneously injected into the right side of the body of a Balb/c mouse. The treatment was started when the long diameter of a tumor reached about 7-9 mm.

The cytokines mIL12, mGMCSF and mIL15 were dissolved in sterile water respectively so that each had a final concentration of 200 ng/μl. 15 μl of each of these cytokine aqueous solutions was taken and mixed to obtain 45 μl of the mIL12+mGMCSF+mIL15 mixture solution, then 45 μl of 3% chitosan quaternary ammonium salt solution prepared in advance was added, and the final solution was carefully pipetted for blending. Pentobarbital sodium was injected into the abdominal cavities of the tumor-bearing mice for anesthesia, then a 29G insulin syringe was used to extract and slowly inject the prepared cytokine chitosan quaternary ammonium salt solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

Figure 9:
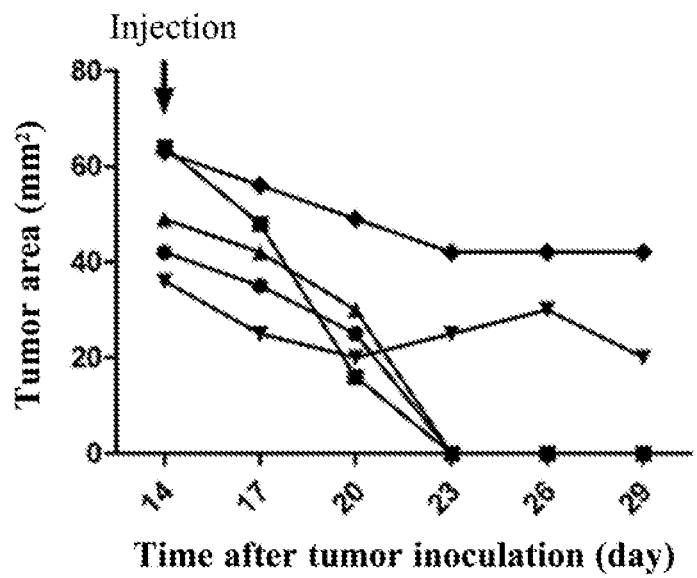
FIG. 9 shows the therapeutic effect of the mIL12+mGMCSF+mIL15 chitosan quaternary ammonium salt solution on the mouse breast cancer (4T1).

The experimental results are shown in FIG. 9. Tumors of 60% of the mice receiving injection regressed completely, and the growth of tumors in the 40% of the mice was suppressed.

Example 10

The Therapeutic Effect of the mIL12+mGMCSF+mIL21 Chitosan Quaternary Ammonium Salt Solution on the Mouse Breast Cancer The cultured mouse breast cancer cells (4T1) were digested, and $2*10^5$ of these cells were subcutaneously injected into the right side of the body of a Balb/c mouse. The treatment was started when the long diameter of a tumor reached about 7-9 mm.

The cytokines mIL12, mGMCSF and mIL21 were dissolved in sterile water respectively so that each had a final concentration of 200 ng/μl. 15 μl of each of these cytokine aqueous solutions was taken and mixed to obtain 45 μl of the mIL12+mGMCSF+mIL21 mixture solution, then 45 μl of 3% chitosan quaternary ammonium salt solution prepared in advance was added, and the final solution was carefully pipetted for blending. Pentobarbital sodium was injected into the abdominal cavities of the tumor-bearing mice for anesthesia, then a 29G insulin syringe was used to extract and slowly inject the prepared cytokine chitosan quaternary ammonium salt solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

Figure 10:
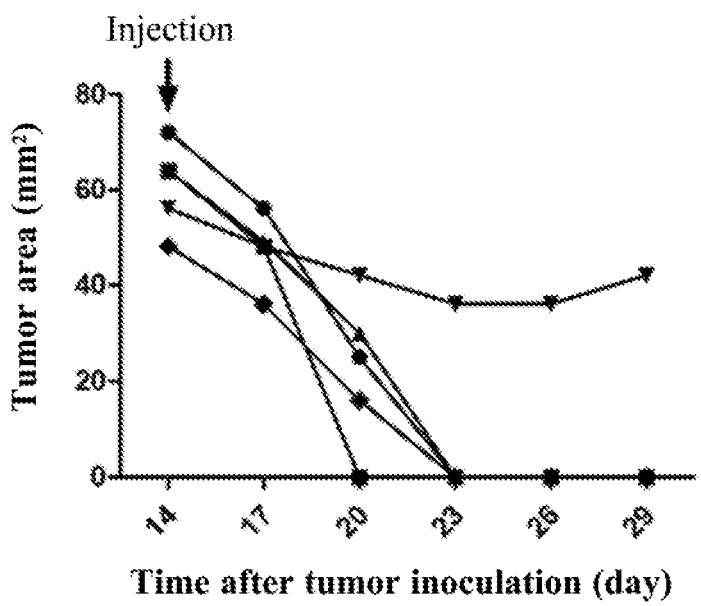
FIG. 10 shows the therapeutic effect of the mIL12+mGMCSF+mIL21 chitosan quaternary ammonium salt solution on the mouse breast cancer (4T1).

The experimental results are shown in FIG. 10. Tumors of 80% of the mice receiving injection regressed completely, and the growth of tumors in the 20% of the mice was suppressed.

Example 11

The Therapeutic Effect of the mIL12+mFLT3L+mIL2 Chitosan Quaternary Ammonium Salt Solution on the Mouse Breast Cancer The cultured mouse breast cancer cells (4T1) were digested, and $2*10^5$ of these cells were subcutaneously injected into the right side of the body of a Balb/c mouse. The treatment was started when the long diameter of a tumor reached about 7-9 mm.

The cytokines mIL12, mFLT3L and mIL2 were dissolved in sterile water respectively so that each had a final concentration of 200 ng/μl. 15 μl of each of these cytokine aqueous solutions was taken and mixed to obtain 45 μl of the mIL12+mFLT3L+mIL2 mixture solution, then 45 μl of 3% chitosan quaternary ammonium salt solution prepared in advance was added, and the final solution was carefully pipetted for blending. Pentobarbital sodium was injected into the abdominal cavities of the tumor-bearing mice for anesthesia, then a 29G insulin syringe was used to extract and slowly inject the prepared cytokine chitosan quaternary ammonium salt solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

Figure 11:
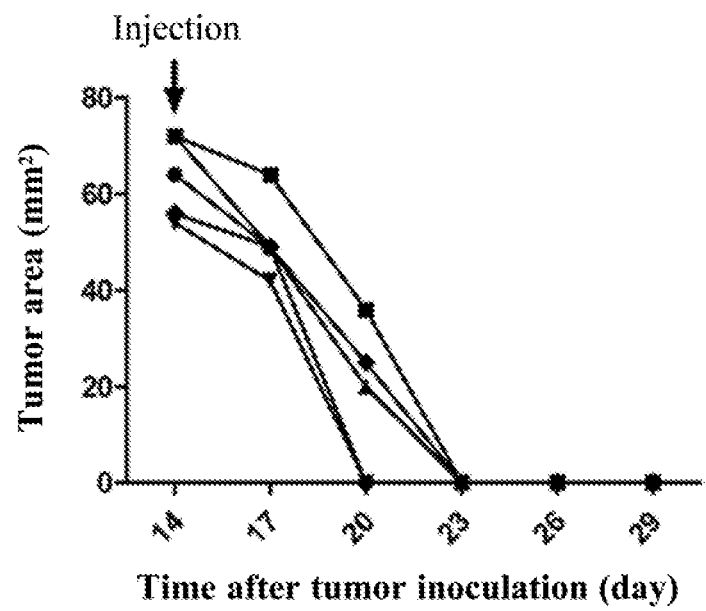
FIG. 11 shows the therapeutic effect of the mIL12+mFLT3L+mIL2 chitosan quaternary ammonium salt solution on the mouse breast cancer (4T1).

The experimental results are shown in FIG. 11. Tumors of all the mice receiving injection regressed completely.

Example 12

The Therapeutic Effect of the mIL12+mFLT3L+mIL15 Chitosan Quaternary Ammonium Salt Solution on the Mouse Breast Cancer The cultured mouse breast cancer cells (4T1) were digested, and $2*10^5$ of these cells were subcutaneously injected into the right side of the body of a Balb/c mouse. The treatment was started when the long diameter of a tumor reached about 7-9 mm.

The cytokines mIL12, mFLT3L and mIL15 were dissolved in sterile water respectively so that each had a final concentration of 200 ng/μl. 15 μl of each of these cytokine aqueous solutions was taken and mixed to obtain 45 μl of the mIL12+mFLT3L+mIL15 mixture solution, then 45 μl of 3% chitosan quaternary ammonium salt solution prepared in advance was added, and the final solution was carefully pipetted for blending. Pentobarbital sodium was injected into the abdominal cavities of the tumor-bearing mice for anesthesia, then a 29G insulin syringe was used to extract and slowly inject the prepared cytokine chitosan quaternary ammonium salt solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

Figure 12:
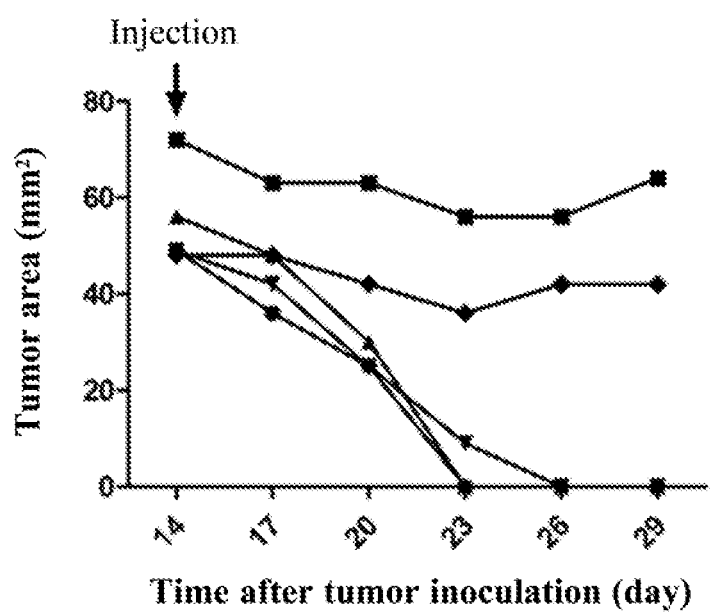
FIG. 12 shows the therapeutic effect of the mIL12+mFLT3L+mIL15 chitosan quaternary ammonium salt solution on the mouse breast cancer (4T1).

The experimental results are shown in FIG. 12. Tumors of 60% of the mice receiving injection regressed completely, and the growth of tumors in the 40% of the mice was suppressed.

Example 13

The Therapeutic Effect of the mIL12+mFLT3L+mIL21 Chitosan Quaternary Ammonium Salt Solution on the Mouse Breast Cancer The cultured mouse breast cancer cells (4T1) were digested, and $2*10^5$ of these cells were subcutaneously injected into the right side of the body of a Balb/c mouse. The treatment was started when the long diameter of a tumor reached about 7-9 mm.

The cytokines mIL12, mFLT3L and mIL21 were dissolved in sterile water respectively so that each had a final concentration of 200 ng/μl. 15 μl of each of these cytokine aqueous solutions was taken and mixed to obtain 45 μl of the mIL12+mFLT3L+mIL21 mixture solution, then 45 μl of 3% chitosan quaternary ammonium salt solution prepared in advance was added, and the final solution was carefully pipetted for blending. Pentobarbital sodium was injected into the abdominal cavities of the tumor-bearing mice for anesthesia, then a 29G insulin syringe was used to extract and slowly inject the prepared cytokine chitosan quaternary ammonium salt solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

Figure 13:
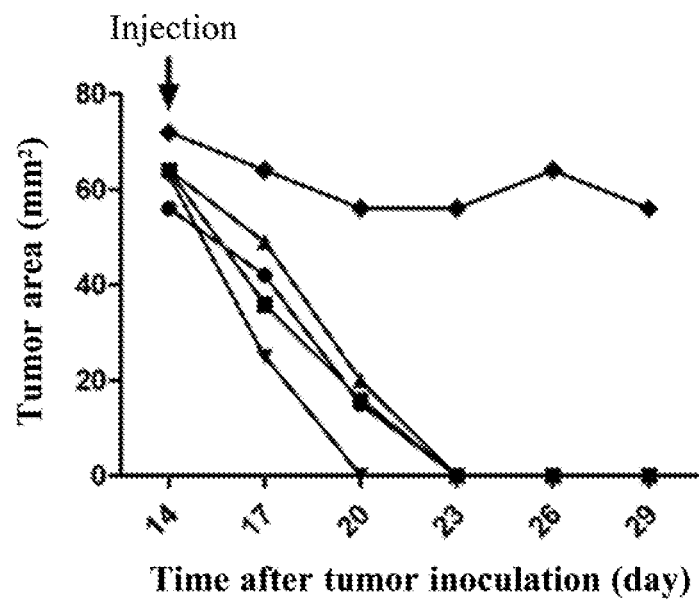
FIG. 13 shows the therapeutic effect of the mIL12+mFLT3L+mIL21 chitosan quaternary ammonium salt solution on the mouse breast cancer (4T1).

The experimental results are shown in FIG. 13. Tumors of 80% of the mice receiving injection regressed completely, and the growth of tumors in the 20% of the mice was suppressed.

Example 14

The Therapeutic Effect of the hIL12+hGMCSF+hIL2 Chitosan Quaternary Ammonium Salt Solution on the Mouse Breast Cancer The cultured mouse breast cancer cells (4T1) were digested, and $2*10^5$ of these cells were subcutaneously injected into the right side of the body of a Balb/c mouse. The treatment was started when the long diameter of a tumor reached about 7-9 mm.

The cytokines hIL12, hGMCSF and hIL2 were dissolved in sterile water respectively so that each had a final concentration of 200 ng/μl. 15 μl of each of these cytokine aqueous solutions was taken and mixed to obtain 45 μl of the hIL12+hGMCSF+hIL2 mixture solution, then 45 μl of 3% chitosan quaternary ammonium salt solution prepared in advance was added, and the final solution was carefully pipetted for blending. Pentobarbital sodium was injected into the abdominal cavities of the tumor-bearing mice for anesthesia, then a 29G insulin syringe was used to extract and slowly inject the prepared cytokine chitosan quaternary ammonium salt solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

Figure 14:
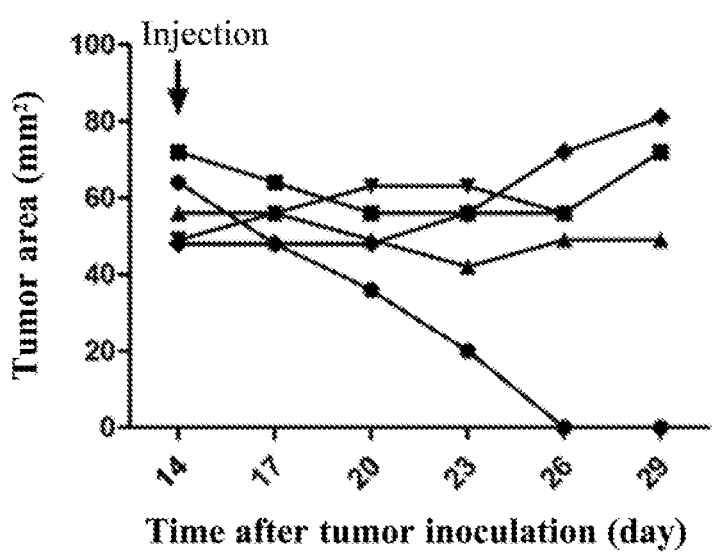
FIG. 14 shows the therapeutic effect of the hIL12+hGMCSF+hIL2 chitosan quaternary ammonium salt solution on the mouse breast cancer (4T1).
Figure 20:
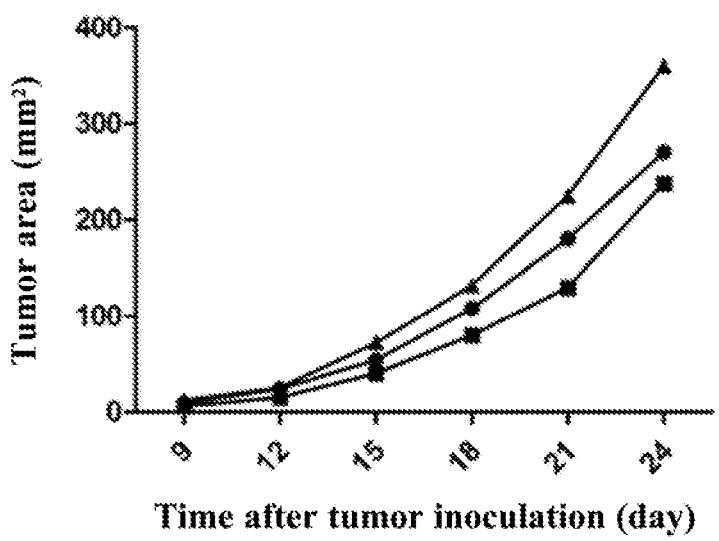
FIG. 20 shows the growth of tumor when the mouse breast cancer (4T1) is not treated.

The experimental results are shown in FIG. 14. Tumors of 20% of the mice receiving injection regressed, and the growth of tumors in the other mice was significantly suppressed as well. Tumors of the untreated mice would rapidly grow, as shown in FIG. 20.

Example 15

The Therapeutic Effect of the hIL12+hGMCSF+hIL15 Chitosan Quaternary Ammonium Salt Solution on the Mouse Breast Cancer The cultured mouse breast cancer cells (4T1) were digested, and $2*10^5$ of these cells were subcutaneously injected into the right side of the body of a Balb/c mouse. The treatment was started when the long diameter of a tumor reached about 7-9 mm.

The cytokines hIL12, hGMCSF and hIL15 were dissolved in sterile water respectively so that each had a final concentration of 200 ng/µl. 15 µl of each of these cytokine aqueous solutions was taken and mixed to obtain 45 µl of the hIL12+hGMCSF+hIL15 mixture solution, then 45 µl of 3% chitosan quaternary ammonium salt solution prepared in advance was added, and the final solution was carefully pipetted for blending. Pentobarbital sodium was injected into the abdominal cavities of the tumor-bearing mice for anesthesia, then a 29G insulin syringe was used to extract and slowly inject the prepared cytokine chitosan quaternary ammonium salt solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

Figure 15:
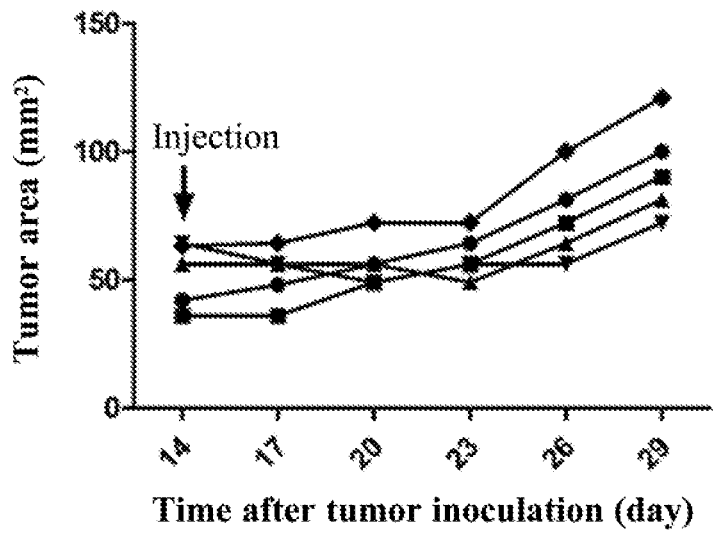
FIG. 15 shows the therapeutic effect of the hIL12+hGMCSF+hIL15 chitosan quaternary ammonium salt solution on the mouse breast cancer (4T1).

The experimental results are shown in FIG. 15. The growth of tumors in all mice receiving injection was significantly suppressed.

Example 16

The Therapeutic Effect of the hIL12+hGMCSF+hIL21 Chitosan Quaternary Ammonium Salt Solution on the Mouse Breast Cancer The cultured mouse breast cancer cells (4T1) were digested, and $2*10^5$ of these cells were subcutaneously injected into the right side of the body of a Balb/c mouse. The treatment was started when the long diameter of a tumor reached about 7-9 mm.

The cytokines hIL12, hGMCSF and hIL21 were dissolved in sterile water respectively so that each had a final concentration of 200 ng/µl. 15 µl of each of these cytokine aqueous solutions was taken and mixed to obtain 45 µl of the hIL12+hGMCSF+hIL21 mixture solution, then 45 µl of 3% chitosan quaternary ammonium salt solution prepared in advance was added, and the final solution was carefully pipetted for blending. Pentobarbital sodium was injected into the abdominal cavities of the tumor-bearing mice for anesthesia, then a 29G insulin syringe was used to extract and slowly inject the prepared cytokine chitosan quaternary ammonium salt solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

Figure 16:
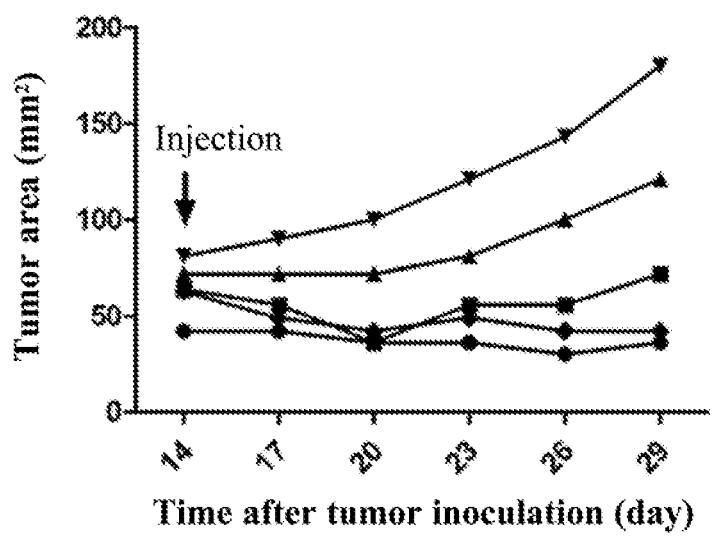
FIG. 16 shows the therapeutic effect of the hIL12+hGMCSF+hIL21 chitosan quaternary ammonium salt solution on the mouse breast cancer (4T1).

The experimental results are shown in FIG. 16. The growth of tumors in all mice receiving injection was significantly suppressed.

Example 17

The Therapeutic Effect of the hIL12+hFLT3L+hIL2 Chitosan Quaternary Ammonium Salt Solution on the Mouse Breast Cancer The cultured mouse breast cancer cells (4T1) were digested, and $2*10^5$ of these cells were subcutaneously injected into the right side of the body of a Balb/c mouse. The treatment was started when the long diameter of a tumor reached about 7-9 mm.

The cytokines hIL12, hFLT3L and hIL2 were dissolved in sterile water respectively so that each had a final concentration of 200 ng/µl. 15 µl of each of these cytokine aqueous solutions was taken and mixed to obtain 45 µl of the hIL12+hFLT3L+hIL2 mixture solution, then 45 µl of 3% chitosan quaternary ammonium salt solution prepared in advance was added, and the final solution was carefully pipetted for blending. Pentobarbital sodium was injected into the abdominal cavities of the tumor-bearing mice for anesthesia, then a 29G insulin syringe was used to extract and slowly inject the prepared cytokine chitosan quaternary ammonium salt solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

Figure 17:
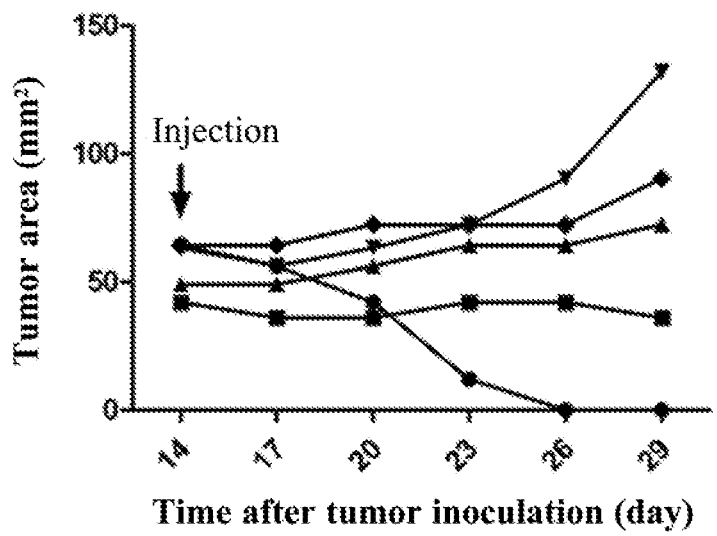
FIG. 17 shows the therapeutic effect of the hIL12+hFLT3L+hIL2 chitosan quaternary ammonium salt solution on the mouse breast cancer (4T1).

The experimental results are shown in FIG. 17. Tumors of 20% of the mice receiving injection regressed, and the growth of tumors in the other mice was significantly suppressed as well.

Example 18

The Therapeutic Effect of the hIL12+hFLT3L+hIL15 Chitosan Quaternary Ammonium Salt Solution on the Mouse Breast Cancer The cultured mouse breast cancer cells (4T1) were digested, and $2*10^5$ of these cells were subcutaneously injected into the right side of the body of a Balb/c mouse. The treatment was started when the long diameter of a tumor reached about 7-9 mm.

The cytokines hIL12, hFLT3L and hIL15 were dissolved in sterile water respectively so that each had a final concentration of 200 ng/µl. 15 µl of each of these cytokine aqueous solutions was taken and mixed to obtain 45 µl of the hIL12+hFLT3L+hIL15 mixture solution, then 45 µl of 3% chitosan quaternary ammonium salt solution prepared in advance was added, and the final solution was carefully pipetted for blending. Pentobarbital sodium was injected into the abdominal cavities of the tumor-bearing mice for anesthesia, then a 29G insulin syringe was used to extract and slowly inject the prepared cytokine chitosan quaternary ammonium salt solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

Figure 18:
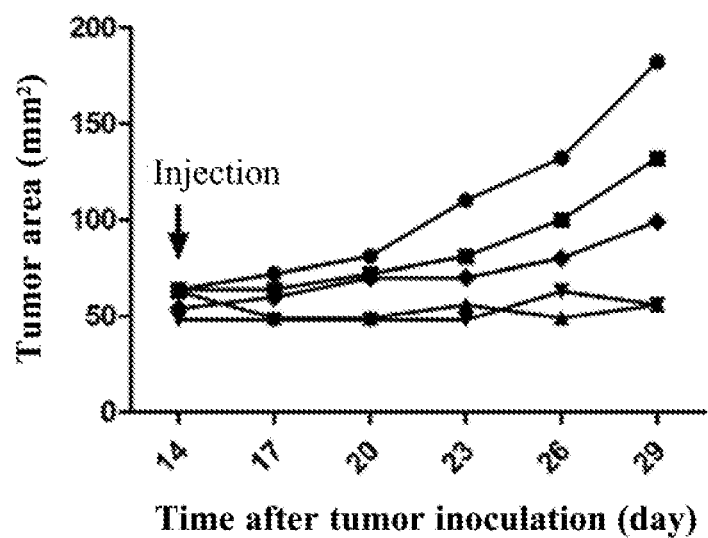
FIG. 18 shows the therapeutic effect of the hIL12+hFLT3L+hIL15 chitosan quaternary ammonium salt solution on the mouse breast cancer (4T1).

The experimental results are shown in FIG. 18. The growth of tumors in all mice receiving injection was significantly suppressed.

Example 19

The Therapeutic Effect of the hIL12+hFLT3L+hIL21 Chitosan Quaternary Ammonium Salt Solution on the Mouse Breast Cancer The cultured mouse breast cancer cells (4T1) were digested, and $2*10^5$ of these cells were subcutaneously injected into the right side of the body of a Balb/c mouse. The treatment was started when the long diameter of a tumor reached about 7-9 mm.

The cytokines hIL12, hFLT3L and hIL21 were dissolved in sterile water respectively so that each had a final concentration of 200 ng/μl. 15 μl of each of these cytokine aqueous solutions was taken and mixed to obtain 45 μl of the hIL12+hFLT3L+hIL21 mixture solution, then 45 μl of 3% chitosan quaternary ammonium salt solution prepared in advance was added, and the final solution was carefully pipetted for blending. Pentobarbital sodium was injected into the abdominal cavities of the tumor-bearing mice for anesthesia, then a 29G insulin syringe was used to extract and slowly inject the prepared cytokine chitosan quaternary ammonium salt solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

Figure 19:
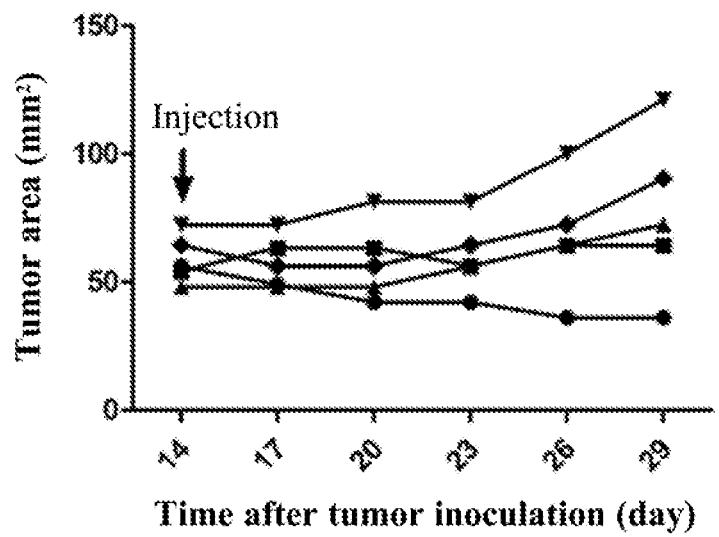
FIG. 19 shows the therapeutic effect of the hIL12+hFLT3L+hIL21 chitosan quaternary ammonium salt solution on the mouse breast cancer (4T1).

The experimental results are shown in FIG. 19. The growth of tumors in all mice receiving injection was significantly suppressed Example 20

Figures 21, 22:
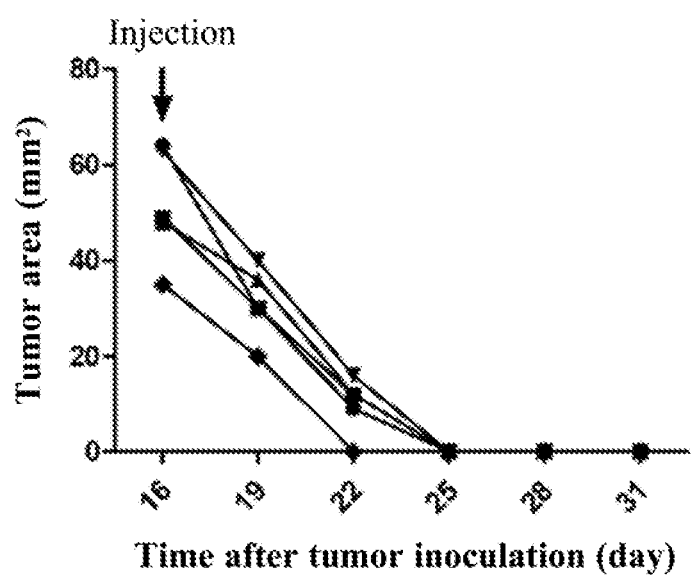
FIG. 21 shows the resisting effect of cured mice on tumor inoculated therein once again.
FIG. 22 shows the therapeutic effect of the mIL12+mGMCSF+mIL7 chitosan quaternary ammonium salt solution on the mouse colon cancer (CT26).

The Resisting Effect of Cured Mouse on Tumor Inoculated Therein Once Again 4 weeks after tumors in the 4T1 tumor-bearing mice that had been treated with the mIL12+mGMCSF+mIL2 chitosan quaternary ammonium salt solutions were regressed, $2*10^5$ 4T1 tumor cells were subcutaneously injected into a side of the body opposite from the side receiving the first tumor inoculation, then the conditions of the mice were observed. The experimental results are shown in FIG. 21. No tumor grew in the mice receiving the second tumor cell injection, while tumors grew in all wild mice that also received the tumor cell injection.

4 weeks after tumors in the CT26 tumor-bearing mice that had been treated with the mIL12+mGMCSF+mIL2 chitosan quaternary ammonium salt solutions were regressed, $2*10^5$ CT26 tumor cells were subcutaneously injected into a side of the body opposite from the side receiving the first tumor inoculation, then the conditions of the mice were observed. The experimental results are shown in FIG. 21. In FIG. 21, "A/B" represents the proportion of the number A of the mice with grown tumors in the number B of the mice injected with the cytokine combination. For example, 2/2 represents that two mice were injected with the cytokine combination and both of them developed with tumors; and 0/5 represents that five mice were injected with the cytokine combination and none of the five mice developed with tumors. The results of FIG. 21 demonstrates that no tumor grew in the mice receiving the second tumor cell injection, while tumors grew in all wild mice that also received the tumor cell injection.

Example 21

The Therapeutic Effect of the mIL12+mGMCSF+mIL7 Chitosan Quaternary Ammonium Salt Solution on the Mouse Colon Cancer The cultured mouse colon cancer cells (CT26) were digested, and $5*10^5$ of these cells were subcutaneously injected into the right side of the body of a Balb/c mouse. The treatment was started when the long diameter of a tumor reached about 7-9 mm.

The cytokines mIL12, mGMCSF and mIL7 were dissolved in sterile water respectively so that each had a final concentration of 150 ng/μl. 15 μl of each of these cytokine aqueous solutions was taken and mixed to obtain 45 μl of the mIL12+mGMCSF+mIL7 mixture solution, then 45 μl of 3% chitosan quaternary ammonium salt solution prepared in advance was added, and the final solution was carefully pipetted for blending. Pentobarbital sodium was injected into the abdominal cavities of the tumor-bearing mice for anesthesia, then a 29G insulin syringe was used to extract and slowly inject the prepared cytokine chitosan quaternary ammonium salt solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

The experimental results are shown in FIG. 22. Tumors of all the mice receiving injection regressed completely.

Example 22

The Therapeutic Effect of the mIL12+mFLT3L+mIL7 Chitosan Quaternary Ammonium Salt Solution on the Mouse Colon Cancer The cultured mouse colon cancer cells (CT26) were digested, and $5*10^5$ of these cells were subcutaneously injected into the right side of the body of a Balb/c mouse. The treatment was started when the long diameter of a tumor reached about 7-9 mm.

The cytokines mIL12, mFLT3L and mIL7 were dissolved in sterile water respectively so that each had a final concentration of 150 ng/μl. 15 μl of each of these cytokine aqueous solutions was taken and mixed to obtain 45 μl of the mIL12+mFLT3L+mIL7 mixture solution, then 45 μl of 3% chitosan quaternary ammonium salt solution prepared in advance was added, and the final solution was carefully pipetted for blending. Pentobarbital sodium was injected into the abdominal cavities of the tumor-bearing mice for anesthesia, then a 29G insulin syringe was used to extract and slowly inject the prepared cytokine chitosan quaternary ammonium salt solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

Figure 23:
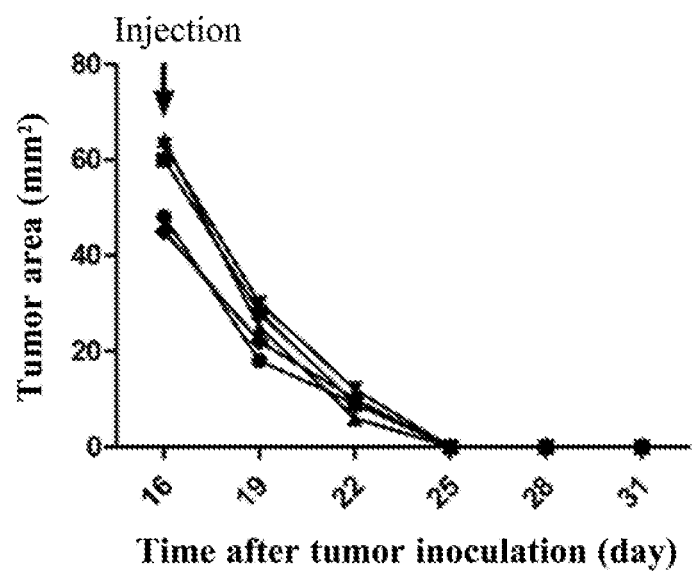
FIG. 23 shows the therapeutic effect of the mIL12+mFLT3L+mIL7 chitosan quaternary ammonium salt solution on the mouse colon cancer (CT26).

The experimental results are shown in FIG. 23. Tumors of all the mice receiving injection regressed completely.

Example 23

The Therapeutic Effect of the hIL12+hGMCSF+hIL7 Chitosan Quaternary Ammonium Salt Solution on the Mouse Colon Cancer The cultured mouse colon cancer cells (CT26) were digested, and $5*10^5$ of these cells were subcutaneously injected into the right side of the body of a Balb/c mouse. The treatment was started when the long diameter of a tumor reached about 7-9 mm.

The cytokines hIL12, hGMCSF and hIL7 were dissolved in sterile water respectively so that each had a final concentration of 300 ng/μl. 15 μl of each of these cytokine aqueous solutions was taken and mixed to obtain 45 μl of the hIL12+hGMCSF+hIL7 mixture solution, then 45 μl of 3% chitosan quaternary ammonium salt solution prepared in advance was added, and the final solution was carefully pipetted for blending. Pentobarbital sodium was injected into the abdominal cavities of the tumor-bearing mice for anesthesia, then a 29G insulin syringe was used to extract and slowly inject the prepared cytokine chitosan quaternary ammonium salt solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

Figure 24:
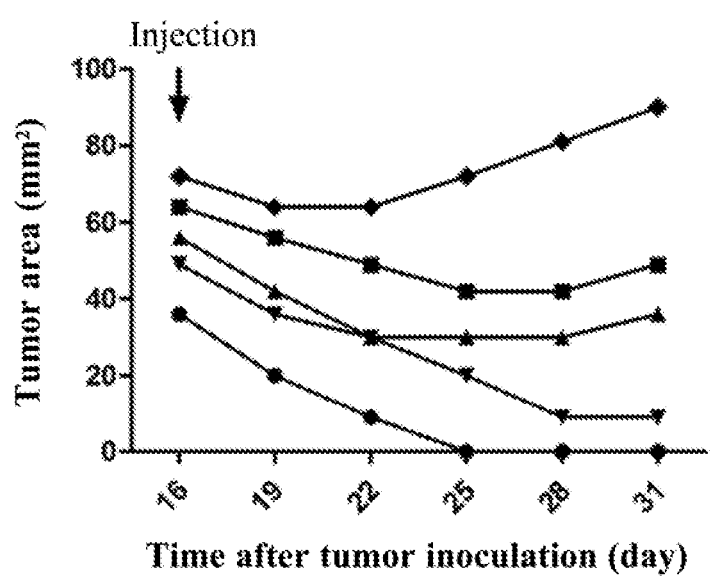
FIG. 24 shows the therapeutic effect of the hIL12+hGMCSF+hIL7 chitosan quaternary ammonium salt solution on the mouse colon cancer (CT26).

The experimental results are shown in FIG. 24. The growth of tumors in all mice receiving injection was significantly suppressed.

Example 24

The Therapeutic Effect of the hIL12+hFLT3L+hIL7 Chitosan Quaternary Ammonium Salt Solution on the Mouse Colon Cancer The cultured mouse colon cancer cells (CT26) were digested, and $5*10^5$ of these cells were subcutaneously injected into the right side of the body of a Balb/c mouse. The treatment was started when the long diameter of a tumor reached about 7-9 mm.

The cytokines hIL12, hFLT3L and hIL7 were dissolved in sterile water respectively so that each had a final concentration of 300 ng/μl. 15 μl of each of these cytokine aqueous solutions was taken and mixed to obtain 45 μl of the hIL12+hFLT3L+hIL7 mixture solution, then 45 μl of 3% chitosan quaternary ammonium salt solution prepared in advance was added, and the final solution was carefully pipetted for blending. Pentobarbital sodium was injected into the abdominal cavities of the tumor-bearing mice for anesthesia, then a 29G insulin syringe was used to extract and slowly inject the prepared cytokine chitosan quaternary ammonium salt solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

Figure 25:
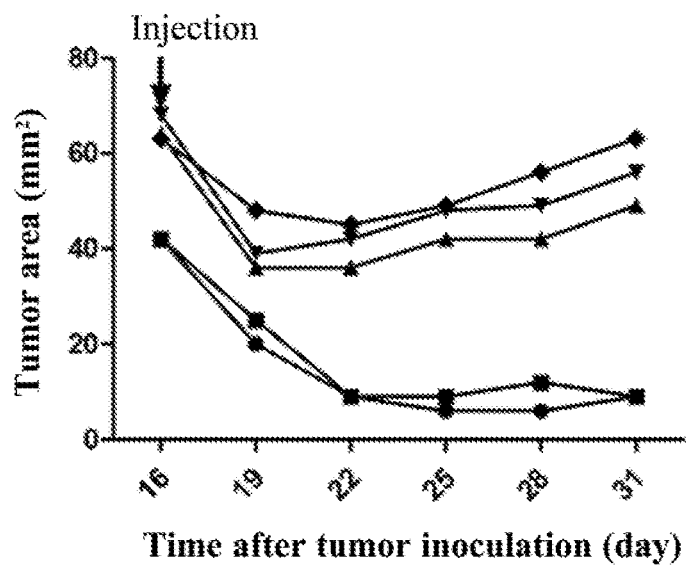
FIG. 25 shows the therapeutic effect of the hIL12+hFLT3L+hIL7 chitosan quaternary ammonium salt solution on the mouse colon cancer (CT26).

The experimental results are shown in FIG. 25. The growth of tumors in all mice receiving injection was significantly suppressed.

Example 25

The Therapeutic Effect of the mIL12 Chitosan Quaternary Ammonium Salt Solution on the Mouse Melanoma The cultured mouse melanoma cells (B16F10) were digested, and $2*10^5$ of these cells were subcutaneously injected into the right side of the body of a C57BL/6 mouse. The treatment was started when the long diameter of a tumor reached about 7-9 mm.

The cytokine mIL12 was dissolved in sterile water so that it had a final concentration of 200 ng/μl. 15 μl of the cytokine aqueous solution was taken and mixed with 45 μl of sterile water, then 45 μl of 3% chitosan quaternary ammonium salt solution prepared in advance was added, and the final solution was carefully pipetted for blending. Pentobarbital sodium was injected into the abdominal cavities of the tumor-bearing mice for anesthesia, then a 29G insulin syringe was used to extract and slowly inject the prepared cytokine chitosan quaternary ammonium salt solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

Figure 26:
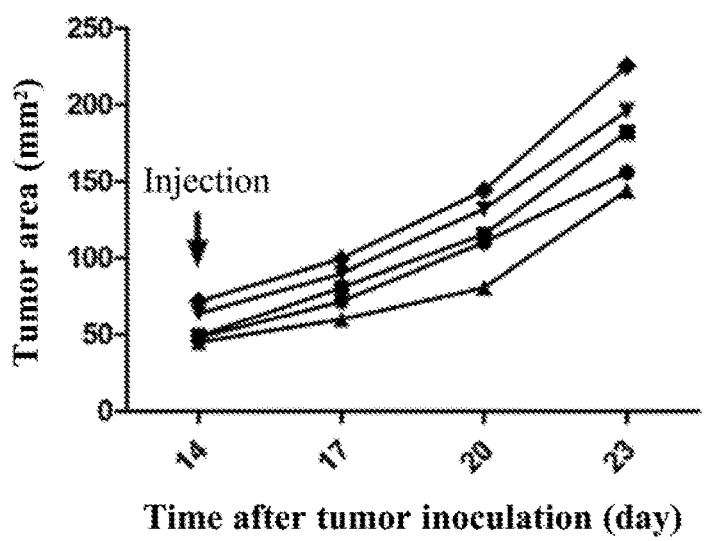
FIG. 26 shows the therapeutic effect of the mIL12 chitosan quaternary ammonium salt solution on the mouse melanoma (B16F10).

The experimental results are shown in FIG. 26. The growth of tumors could not be suppressed by a single IL12.

Example 26

The Therapeutic Effect of the mGMCSF Chitosan Quaternary Ammonium Salt Solution on the Mouse Melanoma The cultured mouse melanoma cells (B16F10) were digested, and $2*10^5$ of these cells were subcutaneously injected into the right side of the body of a C57BL/6 mouse. The treatment was started when the long diameter of a tumor reached about 7-9 mm.

The cytokine mGMCSF was dissolved in sterile water so that it had a final concentration of 200 ng/μl. 15 μl of the cytokine aqueous solution was taken and mixed with 45 μl of sterile water, then 45 μl of 3% chitosan quaternary ammonium salt solution prepared in advance was added, and the final solution was carefully pipetted for blending. Pentobarbital sodium was injected into the abdominal cavities of the tumor-bearing mice for anesthesia, then a 29G insulin syringe was used to extract and slowly inject the prepared cytokine chitosan quaternary ammonium salt solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

Figure 27:
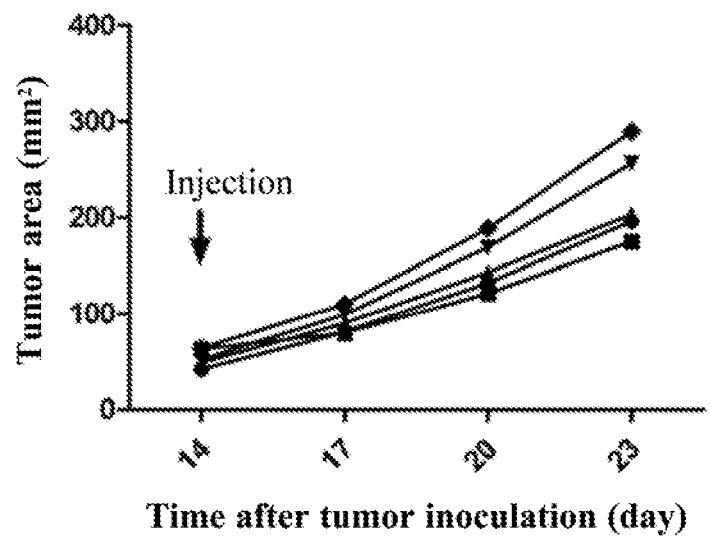
FIG. 27 shows the therapeutic effect of the mGMCSF chitosan quaternary ammonium salt solution on the mouse melanoma (B16F10).

The experimental results are shown in FIG. 27. The growth of tumors could not be suppressed by a single GMCSF.

Example 27

The Therapeutic Effect of the mIL2 Chitosan Quaternary Ammonium Salt Solution on the Mouse Melanoma The cultured mouse melanoma cells (B16F10) were digested, and $2*10^5$ of these cells were subcutaneously injected into the right side of the body of a C57BL/6 mouse. The treatment was started when the long diameter of a tumor reached about 7-9 mm.

The cytokine mIL2 was dissolved in sterile water so that it had a final concentration of 200 ng/μl. 15 μl of the cytokine aqueous solution was taken and mixed with 45 μl of sterile water, then 45 μl of 3% chitosan quaternary ammonium salt solution prepared in advance was added, and the final solution was carefully pipetted for blending. Pentobarbital sodium was injected into the abdominal cavities of the tumor-bearing mice for anesthesia, then a 29G insulin syringe was used to extract and slowly inject the prepared cytokine chitosan quaternary ammonium salt solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

Figure 28:
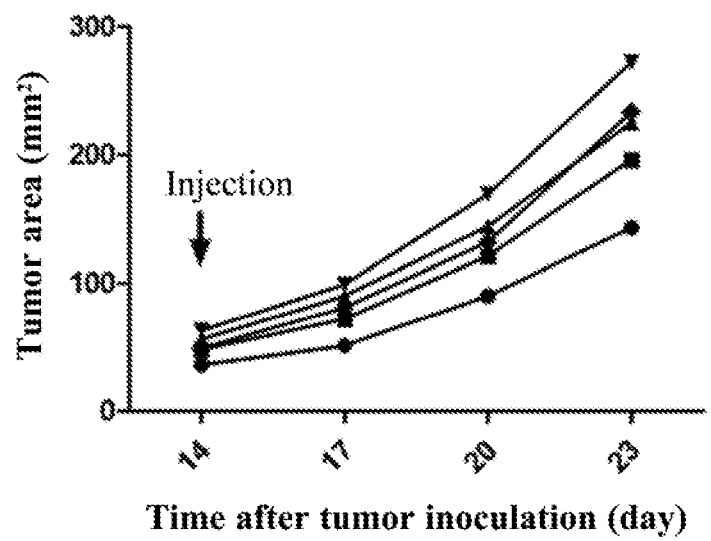
FIG. 28 shows the therapeutic effect of the mIL2 chitosan quaternary ammonium salt solution on the mouse melanoma (B16F10).

The experimental results are shown in FIG. 28. The growth of tumors could not be suppressed by a single IL2.

Example 28

The Therapeutic Effect of the mIL12+mGMCSF Chitosan Quaternary Ammonium Salt Solution on the Mouse Melanoma The cultured mouse melanoma cells (B16F10) were digested, and $2*10^5$ of these cells were subcutaneously injected into the right side of the body of a C57BL/6 mouse. The treatment was started when the long diameter of a tumor reached about 7-9 mm.

The cytokines mIL12 and mGMCSF were dissolved in sterile water respectively so that each had a final concentration of 200 ng/µl. 15 µl of each of these cytokine aqueous solutions was taken and mixed, then 15 µl of sterile water was added to obtain 45 µl of the mIL12+mGMCSF mixture solution, then 45 µl of 3% chitosan quaternary ammonium salt solution prepared in advance was added, and the final solution was carefully pipetted for blending. Pentobarbital sodium was injected into the abdominal cavities of the tumor-bearing mice for anesthesia, then a 29G insulin syringe was used to extract and slowly inject the prepared cytokine chitosan quaternary ammonium salt solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

Figure 29:
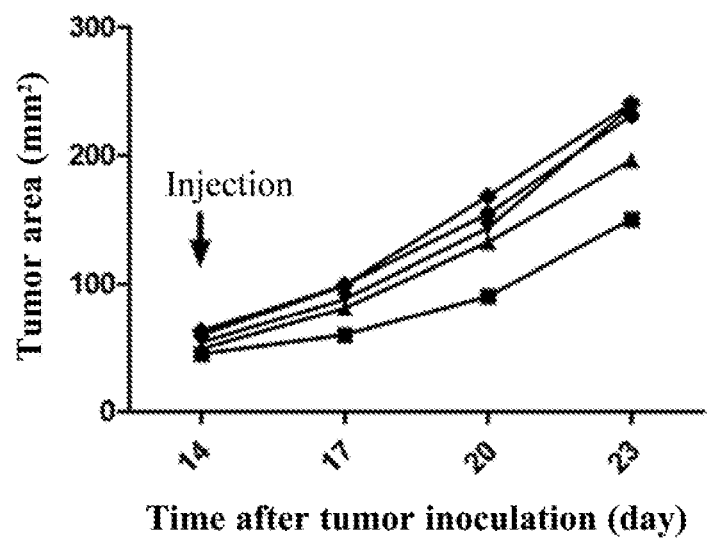
FIG. 29 shows the therapeutic effect of the mIL12+ mGMCSF chitosan quaternary ammonium salt solution on the mouse melanoma (B16F10).

The experimental results are shown in FIG. 29. The growth of tumors could not be suppressed by the combination of IL12 and GMCSF.

Example 29

The Therapeutic Effect of the mIL12+mIL2 Chitosan Quaternary Ammonium Salt Solution on the Mouse Melanoma The cultured mouse melanoma cells (B16F10) were digested, and $2*10^5$ of these cells were subcutaneously injected into the right side of the body of a C57BL/6 mouse. The treatment was started when the long diameter of a tumor reached about 7-9 mm.

The cytokines mIL12 and mIL2 were dissolved in sterile water respectively so that each had a final concentration of 200 ng/µl. 15 µl of each of these cytokine aqueous solutions was taken and mixed, then 15 µl of sterile water was added to obtain 45 µl of the mIL12+mIL2 mixture solution, then 45 µl of 3% chitosan quaternary ammonium salt solution prepared in advance was added, and the final solution was carefully pipetted for blending. Pentobarbital sodium was injected into the abdominal cavities of the tumor-bearing mice for anesthesia, then a 29G insulin syringe was used to extract and slowly inject the prepared cytokine chitosan quaternary ammonium salt solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

Figure 30:
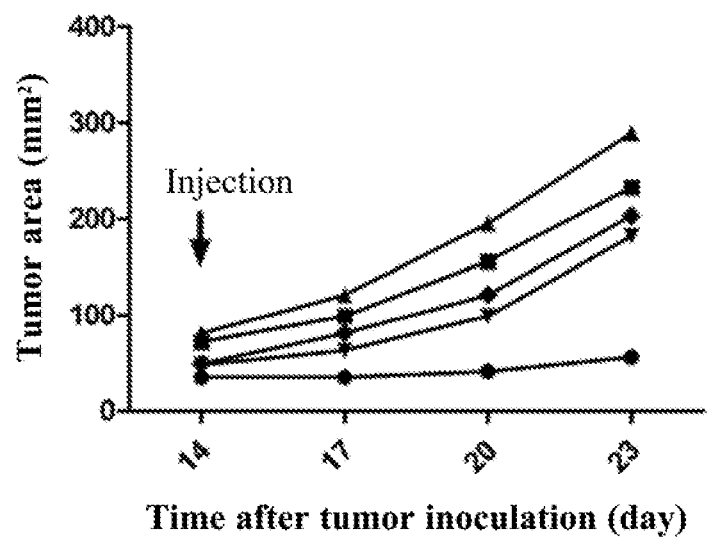
FIG. 30 shows the therapeutic effect of the mIL12+mIL2 chitosan quaternary ammonium salt solution on the mouse melanoma (B16F10).

The experimental results are shown in FIG. 30. The combination of IL12 and IL2 could have a certain suppressing effect in some of the mice, but could not eliminate the tumors.

Example 30

The Therapeutic Effect of the mGMCSF+mIL2 Chitosan Quaternary Ammonium Salt Solution on the Mouse Melanoma The cultured mouse melanoma cells (B16F10) were digested, and $2*10^5$ of these cells were subcutaneously injected into the right side of the body of a C57BL/6 mouse. The treatment was started when the long diameter of a tumor reached about 7-9 mm.

The cytokines mGMCSF and mIL2 were dissolved in sterile water respectively so that each had a final concentration of 200 ng/µl. 15 µl of each of these cytokine aqueous solutions was taken and mixed, then 15 µl of sterile water was added to obtain 45 µl of the mGMCSF+mIL2 mixture solution, then 45 µl of 3% chitosan quaternary ammonium salt solution prepared in advance was added, and the final solution was carefully pipetted for blending. Pentobarbital sodium was injected into the abdominal cavities of the tumor-bearing mice for anesthesia, then a 29G insulin syringe was used to extract and slowly inject the prepared cytokine chitosan quaternary ammonium salt solution into the tumor. After the injection was completed, the syringe needle was detained therein for a short time to reduce the overflow of the solution. The rejected mice were put back into the cage, and kept warm until they woke up. The growth of the tumors in the mice was observed and recorded.

Figure 31:
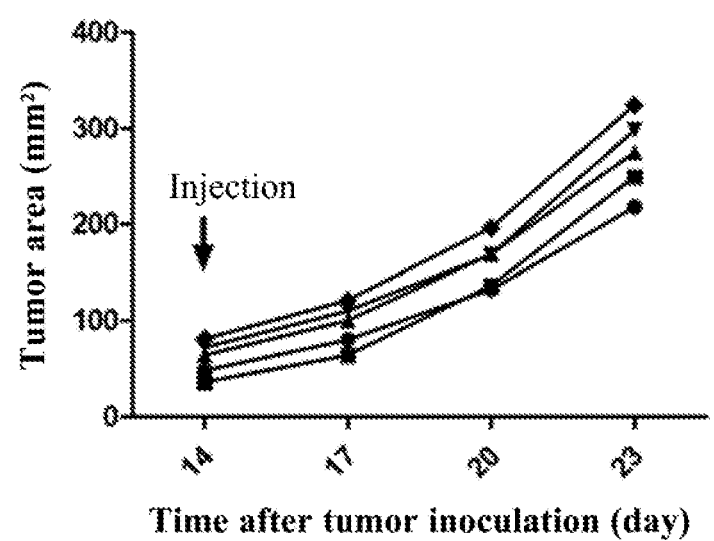
FIG. 31 shows the therapeutic effect of the mGMCSF+ mIL2 chitosan quaternary ammonium salt solution on the mouse melanoma (B16F10).

The experimental results are shown in FIG. 31. The growth of tumors could not be suppressed by the combination of GMCSF and IL2.

The aforementioned detailed description is provided in an explanatory and illustrative manner, and is not intended to limit the scope of the appended claims. So far, a variety of variations of the embodiments illustrated herein are apparent to those of ordinary skill in the art, and falls in the scope of the appended claims and equivalent embodiments thereof.

What is claimed is:

1. A pharmaceutical composition, comprising consisting of interleukin 12 (IL12), granulocyte macrophage colony stimulating factor (GMCSF), and interleukin 2 (IL2), and a pharmaceutically acceptable carrier, wherein the proportion of IL12, GMCSF and IL2 in the pharmaceutical composition is 5:1:1, 1:5:1, 1:1:5 or 1:1:1.

2. The pharmaceutical composition of claim 1, wherein the IL12, GMCSF, and IL2 are selected from the following groups: mouse IL12, GMCSF, and IL2 and human IL12, GMCSF, and IL2.

3. The pharmaceutical composition of claim 1, wherein the concentration of each of IL12, GMCSF, and IL2 in the pharmaceutical composition is 1-10000 ng/L.

4. The pharmaceutical composition of claim 1, prepared to be suitable for slow-release administration.

5. The pharmaceutical composition of claim 1, prepared in a calcium alginate gel, a polylactic acid microsphere or a chitosan quaternary ammonium salt solution.

6. A pharmaceutical composition of claim 1, wherein the proportion of IL12, GMCSF and IL2 in the pharmaceutical composition is 5:1:1, 1:5:1, 1:1:5.

7. The pharmaceutical composition of claim 6, wherein the IL12, GMCSF, and IL2 are selected from the following groups: mouse IL12, GMCSF, and IL2 and human IL12, GMCSF, and IL2.

8. The pharmaceutical composition of claim 6, wherein the concentration of each of IL12, GMCSF, and IL2 in the pharmaceutical composition is 1-10000 ng/L.

9. The pharmaceutical composition of claim 6, prepared to be suitable for slow-release administration.

10. The pharmaceutical composition of claim 6, prepared in a calcium alginate gel, a polylactic acid microsphere or a chitosan quaternary ammonium salt solution.

11. A method of treating tumors and/or preventing the recurrence or metastasis of a tumor in a subject in need thereof, wherein the tumor is a breast cancer, colorectal cancer, skin cancer, or lymphoma, comprising the administration of a therapeutic amount of the cytokine combination of claim 1.

12. The method of claim 11, wherein the concentration of each cytokine in the cytokine combination is 1-10000 ng/L.

13. The method of claim 11, wherein the subject is a mammal.

14. The method of claim 13, wherein said mammal is selected from the group consisting of human being, mouse, rat, monkey, dog, pig, sheep, cow and cat.

\* \* \* \* \*

SEQUENCE LISTING

<160> NUMBER OF SEQ ID NOS: 16

<210> SEQ ID NO 1
<211> LENGTH: 193
<212> TYPE: PRT
<213> ORGANISM: Mus musculus

<400> SEQUENCE: 1

```
Arg Val Ile Pro Val Ser Gly Pro Ala Arg Cys Leu Ser Gln Ser Arg
1               5                   10                  15
Asn Leu Leu Lys Thr Thr Asp Asp Met Val Lys Thr Ala Arg Glu Lys
            20                  25                  30
Leu Lys His Tyr Ser Cys Thr Ala Glu Asp Ile Asp His Glu Asp Ile
            35                  40                  45
Thr Arg Asp Gln Thr Ser Thr Leu Lys Thr Cys Leu Pro Leu Glu Leu
50                  55                  60
His Lys Asn Glu Ser Cys Leu Ala Thr Arg Glu Thr Ser Ser Thr Thr
65                  70                  75                  80
Arg Gly Ser Cys Leu Pro Pro Gln Lys Thr Ser Leu Met Met Thr Leu
                85                  90                  95
Cys Leu Gly Ser Ile Tyr Glu Asp Leu Lys Met Tyr Gln Thr Glu Phe
                100                 105                 110
Gln Ala Ile Asn Ala Ala Leu Gln Asn His Asn His Gln Ile Ile
                115                 120                 125
Leu Asp Lys Gly Met Leu Val Ala Ile Asp Glu Leu Met Gln Ser Leu
            130                 135                 140
Asn His Asn Gly Glu Thr Leu Arg Gln Lys Pro Pro Val Gly Glu Ala
145                 150                 155                 160
Asp Pro Tyr Arg Val Lys Met Lys Leu Cys Ile Leu Leu His Ala Phe
                165                 170                 175
Ser Thr Arg Val Val Thr Ile Asn Arg Val Met Gly Tyr Leu Ser Ser
                180                 185                 190
Ala

<210> SEQ ID NO 2
<211> LENGTH: 313
<212> TYPE: PRT
<213> ORGANISM: Mus musculus

<400> SEQUENCE: 2

Met Trp Glu Leu Glu Lys Asp Val Tyr Val Val Glu Val Asp Trp Thr
1               5                   10                  15
Pro Asp Ala Pro Gly Glu Thr Val Asn Leu Thr Cys Asp Thr Pro Glu
            20                  25                  30
Glu Asp Asp Ile Thr Trp Thr Ser Asp Gln Arg His Gly Val Ile Gly
            35                  40                  45
Ser Gly Lys Thr Leu Thr Ile Thr Val Lys Glu Phe Leu Asp Ala Gly
50                  55                  60
Gln Tyr Thr Cys His Lys Gly Gly Glu Thr Leu Ser His Ser His Leu
65                  70                  75                  80
Leu Leu His Lys Lys Glu Asn Gly Ile Trp Ser Thr Glu Ile Leu Lys
                85                  90                  95
Asn Phe Lys Asn Lys Thr Phe Leu Lys Cys Glu Ala Pro Asn Tyr Ser
                100                 105                 110
Gly Arg Phe Thr Cys Ser Trp Leu Val Gln Arg Asn Met Asp Leu Lys
                115                 120                 125
Phe Asn Ile Lys Ser Ser Ser Ser Pro Asp Ser Arg Ala Val Thr
            130                 135                 140
Cys Gly Met Ala Ser Leu Ser Ala Glu Lys Val Thr Leu Asp Gln Arg
145                 150                 155                 160
Asp Tyr Glu Lys Tyr Ser Val Ser Cys Gln Glu Asp Val Thr Cys Pro
                165                 170                 175
```

```
Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser
305                 310

<210> SEQ ID NO 3
<211> LENGTH: 124
<212> TYPE: PRT
<213> ORGANISM: Mus musculus

<400> SEQUENCE: 3

Ala Pro Thr Arg Ser Pro Ile Thr Val Thr Arg Pro Trp Lys His Val
1               5                   10                  15

Glu Ala Ile Lys Glu Ala Leu Asn Leu Leu Asp Asp Met Pro Val Thr
            20                  25                  30

Leu Asn Glu Glu Val Glu Val Val Ser Asn Glu Phe Ser Phe Lys Lys
        35                  40                  45

Leu Thr Cys Val Gln Thr Arg Leu Lys Ile Phe Glu Gln Gly Leu Arg
    50                  55                  60

Gly Asn Phe Thr Lys Leu Lys Gly Ala Leu Asn Met Thr Ala Ser Tyr
65                  70                  75                  80

Tyr Gln Thr Tyr Cys Pro Pro Thr Pro Glu Thr Asp Cys Glu Thr Gln
                85                  90                  95

Val Thr Thr Tyr Ala Asp Phe Ile Asp Ser Leu Lys Thr Phe Leu Thr
            100                 105                 110

Asp Ile Pro Phe Glu Cys Lys Lys Pro Gly Gln Lys
        115                 120

<210> SEQ ID NO 4
<211> LENGTH: 206
<212> TYPE: PRT
<213> ORGANISM: Mus musculus

<400> SEQUENCE: 4

Gly Thr Pro Asp Cys Tyr Phe Ser His Ser Pro Ile Ser Ser Asn Phe
1               5                   10                  15

Lys Val Lys Phe Arg Glu Leu Thr Asp His Leu Leu Lys Asp Tyr Pro
            20                  25                  30

Val Thr Val Ala Val Asn Leu Gln Asp Glu Lys His Cys Lys Ala Leu
        35                  40                  45

Trp Ser Leu Phe Leu Ala Gln Arg Trp Ile Glu Gln Leu Lys Thr Val
    50                  55                  60
```

Ala Gly Ser Lys Met Gln Thr Leu Leu Glu Asp Val Asn Thr Glu Ile
65                  70                  75                  80

His Phe Val Thr Ser Cys Thr Phe Gln Pro Leu Pro Glu Cys Leu Arg
                85                  90                  95

Phe Val Gln Thr Asn Ile Ser His Leu Leu Lys Asp Thr Cys Thr Gln
            100                 105                 110

Leu Leu Ala Leu Lys Pro Cys Ile Gly Lys Ala Cys Gln Asn Phe Ser
        115                 120                 125

Arg Cys Leu Glu Val Gln Cys Gln Pro Asp Ser Ser Thr Leu Leu Pro
    130                 135                 140

Pro Arg Ser Pro Ile Ala Leu Glu Ala Thr Glu Leu Pro Glu Pro Arg
145                 150                 155                 160

Pro Arg Gln Leu Leu Leu Leu Leu Leu Leu Leu Pro Leu Thr Leu
                165                 170                 175

Val Leu Leu Ala Ala Ala Trp Gly Leu Arg Trp Gln Arg Ala Arg Arg
                180                 185                 190

Arg Gly Glu Leu His Pro Gly Val Pro Leu Pro Ser His Pro
            195                 200                 205

<210> SEQ ID NO 5
<211> LENGTH: 149
<212> TYPE: PRT
<213> ORGANISM: Mus musculus

<400> SEQUENCE: 5

Ala Pro Thr Ser Ser Thr Ser Ser Ser Thr Ala Glu Ala Gln Gln
1               5                   10                  15

Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
            35                  40                  45

Lys Leu Pro Arg Met Leu Thr Phe Lys Phe Tyr Leu Pro Lys Gln Ala
    50                  55                  60

Thr Glu Leu Lys Asp Leu Gln Cys Leu Glu Asp Glu Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Ser Ala Thr
        115                 120                 125

Val Val Asp Phe Leu Arg Arg Trp Ile Ala Phe Cys Gln Ser Ile Ile
    130                 135                 140

Ser Thr Ser Pro Gln
145

<210> SEQ ID NO 6
<211> LENGTH: 114
<212> TYPE: PRT
<213> ORGANISM: Mus musculus

<400> SEQUENCE: 6

Asn Trp Ile Asp Val Arg Tyr Asp Leu Glu Lys Ile Glu Ser Leu Ile
1               5                   10                  15

Gln Ser Ile His Ile Asp Thr Thr Leu Tyr Thr Asp Ser Asp Phe His
            20                  25                  30

```
Pro Ser Cys Lys Val Thr Ala Met Asn Cys Phe Leu Leu Glu Leu Gln
            35                  40                  45

Val Ile Leu His Glu Tyr Ser Asn Met Thr Leu Asn Glu Thr Val Arg
 50                  55                  60

Asn Val Leu Tyr Leu Ala Asn Ser Thr Leu Ser Ser Asn Lys Asn Val
 65                  70                  75                  80

Ala Glu Ser Gly Cys Lys Cys Glu Glu Leu Glu Glu Lys Thr Phe
                85                  90                  95

Thr Glu Phe Leu Gln Ser Phe Ile Arg Ile Val Gln Met Phe Ile Asn
                100                 105                 110

Thr Ser

<210> SEQ ID NO 7
<211> LENGTH: 129
<212> TYPE: PRT
<213> ORGANISM: Mus musculus

<400> SEQUENCE: 7

His Lys Ser Ser Pro Gln Gly Pro Asp Arg Leu Leu Ile Arg Leu Arg
 1               5                  10                  15

His Leu Ile Asp Ile Val Glu Gln Leu Lys Ile Tyr Glu Asn Asp Leu
                20                  25                  30

Asp Pro Glu Leu Leu Ser Ala Pro Gln Asp Val Lys Gly His Cys Glu
            35                  40                  45

His Ala Ala Phe Ala Cys Phe Gln Lys Ala Lys Leu Lys Pro Ser Asn
 50                  55                  60

Pro Gly Asn Asn Lys Thr Phe Ile Ile Asp Leu Val Ala Gln Leu Arg
 65                  70                  75                  80

Arg Arg Leu Pro Ala Arg Arg Gly Gly Lys Lys Gln Lys His Ile Ala
                85                  90                  95

Lys Cys Pro Ser Cys Asp Ser Tyr Glu Lys Arg Thr Pro Lys Glu Phe
                100                 105                 110

Leu Glu Arg Leu Lys Trp Leu Leu Gln Lys Met Ile His Gln His Leu
            115                 120                 125

Ser

<210> SEQ ID NO 8
<211> LENGTH: 197
<212> TYPE: PRT
<213> ORGANISM: Homo sapiens

<400> SEQUENCE: 8

Arg Asn Leu Pro Val Ala Thr Pro Asp Pro Gly Met Phe Pro Cys Leu
 1               5                  10                  15

His His Ser Gln Asn Leu Leu Arg Ala Val Ser Asn Met Leu Gln Lys
                20                  25                  30

Ala Arg Gln Thr Leu Glu Phe Tyr Pro Cys Thr Ser Glu Glu Ile Asp
            35                  40                  45

His Glu Asp Ile Thr Lys Asp Lys Thr Ser Thr Val Glu Ala Cys Leu
 50                  55                  60

Pro Leu Glu Leu Thr Lys Asn Glu Ser Cys Leu Asn Ser Arg Glu Thr
 65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
                100                 105                 110
```

```
Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195

<210> SEQ ID NO 9
<211> LENGTH: 306
<212> TYPE: PRT
<213> ORGANISM: Homo sapiens

<400> SEQUENCE: 9

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
                20                  25                  30

Glu Asp Gly Ile Thr Trp Thr Leu Asp Gln Ser Ser Glu Val Leu Gly
            35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
```

```
                    275                 280                 285

Gln Asp Arg Tyr Tyr Ser Ser Ser Trp Ser Glu Trp Ala Ser Val Pro
    290                 295                 300

Cys Ser
305

<210> SEQ ID NO 10
<211> LENGTH: 127
<212> TYPE: PRT
<213> ORGANISM: Homo sapiens

<400> SEQUENCE: 10

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125

<210> SEQ ID NO 11
<211> LENGTH: 209
<212> TYPE: PRT
<213> ORGANISM: Homo sapiens

<400> SEQUENCE: 11

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Gln Pro Asp Ser Ser Thr Leu Pro Pro Pro Trp Ser
    130                 135                 140

Pro Arg Pro Leu Glu Ala Thr Ala Pro Thr Ala Pro Gln Pro Pro Leu
145                 150                 155                 160

Leu Leu Leu Leu Leu Leu Pro Val Gly Leu Leu Leu Leu Ala Ala Ala
```

```
                165                 170                 175
Trp Cys Leu His Trp Gln Arg Thr Arg Arg Thr Pro Arg Pro Gly
            180                 185                 190

Glu Gln Val Pro Val Pro Ser Pro Gln Asp Leu Leu Val Glu
        195                 200                 205

His

<210> SEQ ID NO 12
<211> LENGTH: 133
<212> TYPE: PRT
<213> ORGANISM: Homo sapiens

<400> SEQUENCE: 12

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 13
<211> LENGTH: 114
<212> TYPE: PRT
<213> ORGANISM: Homo sapiens

<400> SEQUENCE: 13

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 14
<211> LENGTH: 133
```

```
<212> TYPE: PRT
<213> ORGANISM: Homo sapiens

<400> SEQUENCE: 14

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
    130

<210> SEQ ID NO 15
<211> LENGTH: 129
<212> TYPE: PRT
<213> ORGANISM: Mus musculus

<400> SEQUENCE: 15

Glu Cys His Ile Lys Asp Lys Glu Gly Lys Ala Tyr Glu Ser Val Leu
1               5                   10                  15

Met Ile Ser Ile Asp Glu Leu Asp Lys Met Thr Gly Thr Asp Ser Asn
            20                  25                  30

Cys Pro Asn Asn Glu Pro Asn Phe Phe Arg Lys His Val Cys Asp Asp
        35                  40                  45

Thr Lys Glu Ala Ala Phe Leu Asn Arg Ala Ala Arg Lys Leu Lys Gln
    50                  55                  60

Phe Leu Lys Met Asn Ile Ser Glu Glu Phe Asn Val His Leu Leu Thr
65                  70                  75                  80

Val Ser Gln Gly Thr Gln Thr Leu Val Asn Cys Thr Ser Lys Glu Glu
                85                  90                  95

Lys Asn Val Lys Glu Gln Lys Lys Asn Asp Ala Cys Phe Leu Lys Arg
            100                 105                 110

Leu Leu Arg Glu Ile Lys Thr Cys Trp Asn Lys Ile Leu Lys Gly Ser
        115                 120                 125

Ile

<210> SEQ ID NO 16
<211> LENGTH: 152
<212> TYPE: PRT
<213> ORGANISM: Homo sapiens

<400> SEQUENCE: 16

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30
```

```
Asn Cys Leu Asn Asn Glu Phe Asn Phe Phe Lys Arg His Ile Cys Asp
        35              40              45
Ala Asn Lys Glu Gly Met Phe Leu Phe Arg Ala Ala Arg Lys Leu Arg
        50              55              60
Gln Phe Leu Lys Met Asn Ser Thr Gly Asp Phe Asp Leu His Leu Leu
 65              70              75              80
Lys Val Ser Glu Gly Thr Thr Ile Leu Leu Asn Cys Thr Gly Gln Val
            85              90              95
Lys Gly Arg Lys Pro Ala Ala Leu Gly Glu Ala Gln Pro Thr Lys Ser
            100             105             110
Leu Glu Glu Asn Lys Ser Leu Lys Glu Gln Lys Lys Leu Asn Asp Leu
        115             120             125
Cys Phe Leu Lys Arg Leu Leu Gln Glu Ile Lys Thr Cys Trp Asn Lys
        130             135             140
Ile Leu Met Gly Thr Lys Glu His
145             150
```